US012702269B2

(12) United States Patent
Fujii

(10) Patent No.: US 12,702,269 B2
(45) Date of Patent: Aug. 11, 2026

(54) IMAGE PROCESSING APPARATUS, IMAGE PROCESSING METHOD, NAVIGATION METHOD AND ENDOSCOPE SYSTEM

(71) Applicant: OLYMPUS CORPORATION, Tokyo (JP)

(72) Inventor: Toshiyuki Fujii, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 735 days.

(21) Appl. No.: 17/960,983

(22) Filed: Oct. 6, 2022

(65) Prior Publication Data

US 2023/0039047 A1 Feb. 9, 2023

Related U.S. Application Data

(63) Continuation of application No. PCT/JP2020/016037, filed on Apr. 9, 2020.

(51) Int. Cl.

*A61B 1/00* (2006.01)
*A61B 1/06* (2006.01)
*G06T 7/00* (2017.01)

(52) U.S. Cl.

CPC ...... *A61B 1/00009* (2013.01); *A61B 1/00006* (2013.01); *A61B 1/0661* (2013.01); *G06T 7/0012* (2013.01); *G06T 2207/10068* (2013.01)

(58) Field of Classification Search

CPC ............ A61B 1/00009; A61B 1/00006; A61B 1/0661; A61B 1/000094; A61B 1/000095;

(Continued)

(56) References Cited

U.S. PATENT DOCUMENTS

2009/0192348 A1* 7/2009 Nishino ................. A61B 1/041 600/103
2014/0303435 A1 10/2014 Taniguchi (Continued)

FOREIGN PATENT DOCUMENTS

CN 104114077 A 10/2014
CN 106659360 A 5/2017

(Continued)

OTHER PUBLICATIONS

International Search Report dated Jun. 30, 2020 issued in PCT/JP2020/016037.

*Primary Examiner* — Ross Varndell
*Assistant Examiner* — Rachel L Roberts
(74) *Attorney, Agent, or Firm* — Scully, Scott, Murphy & Presser, P.C.

(57) ABSTRACT

An image processing apparatus includes a processor including hardware. The processor is configured to: set a first acquisition condition and a second acquisition condition for a video processor configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition; generate support information based on an image analysis result; and control switching between the first acquisition condition and the second acquisition condition according to the image analysis result.

13 Claims, 13 Drawing Sheets

(58) Field of Classification Search
CPC ... A61B 1/0638; A61B 1/0655; A61B 1/3132; A61B 1/045; G06T 7/0012; G06T 2207/10068
See application file for complete search history.

(56) References Cited

U.S. PATENT DOCUMENTS

| | | | | |
|---|---|---|---|---|
| 2017/0086659 | A1 | 3/2017 | Uchiyama et al. | |
| 2017/0112356 | A1 | 4/2017 | Mitsui et al. | |
| 2019/0073768 | A1 | 3/2019 | Shigeta | |
| 2019/0282135 | A1* | 9/2019 | Ito | A61B 1/044 |
| 2020/0008653 | A1* | 1/2020 | Kamon | A61B 1/00055 |
| 2020/0015927 | A1 | 1/2020 | Ichiki et al. | |

FOREIGN PATENT DOCUMENTS

| | | | | |
|---|---|---|---|---|
| EP | 3449799 | A1 | 3/2019 | |
| JP | 2012011238 | A | 1/2012 | |
| JP | 2016-019569 | A | 2/2016 | |
| JP | 2019042156 | A | 3/2019 | |
| WO | 2018163644 | A1 | 9/2018 | |
| WO | WO-2019220859 | A1 * | 11/2019 | G06V 10/751 |

* cited by examiner

FIG. 2

| CATEGORY | HUMAN BEING<br>⇒ LOW INFORMATION PROCESSING SPEED<br>⇒ WISHES TO BE PROVIDED WITH USEFUL INFORMATION ONLY | NAVIGATION APPARATUS (COMPUTER)<br>⇒ HIGH INFORMATION PROCESSING SPEED<br>⇒ MORE EASILY ACQUIRES USEFUL INFORMATION AS AMOUNT OF INFORMATION IS LARGER |
|---|---|---|
| IMAGE QUALITY | WISHES ONLY SITE OF INTEREST TO BE CONSPICUOUS BECAUSE CONSPICUOUS PART OTHER THAN SITE OF INTEREST IS DISTRACTING<br>WISHES TO BE PROVIDED WITH IMAGE CLOSE TO VISUAL OBSERVATION<br>· LESS NOISE IS BETTER<br>· GAMMA PROCESSING PERFORMED SO AS TO BE CLOSE TO HUMAN EYES<br>· FOR ENHANCEMENT, ENHANCE FREQUENCY BAND TO BE VIEWED | ONLY SMALL ADVERSE IMPACT OF CONSPICUOUS PART OTHER THAN SITE OF INTEREST<br>· INFORMATION USEFUL FOR NAVIGATION APPARATUS MAY BE REMOVED BY NOISE REDUCTION, GAMMA PROCESSING, AND IMAGE ENHANCEMENT ALTHOUGH HUMAN BEING IS UNAWARE OF SUCH REMOVAL |
| SPECIAL IMAGES (NBI, ETC.) | WISHES TO VIEW ONLY ONE TYPE OF SPECIAL IMAGE OR WISHES SPECIAL IMAGE TO BE SUPERIMPOSED | NO PROBLEM IN SEVERAL TYPES OF IMAGES BEING CONTINUOUSLY INPUTTED |
| FRAME RATE | FEELS STRESS IF FRAME RATE IS NOT 30 FPS OR MORE | HAS NO RESTRICTION<br>NO PROBLEM WITH RELATIVELY LOW FRAME RATE (AROUND 1 FPS) IF FRAME RATE IS SUFFICIENT NOT TO MISS USEFUL INFORMATION |

FIG. 9

| CATEGORY | DISPLAY-PURPOSE ACQUISITION CONDITION | ANALYSIS-PURPOSE ACQUISITION CONDITION |
|---|---|---|
| GAMMA | GAMMA PROCESSING SUITED TO HUMAN EYES | PERFORM NO GAMMA PROCESSING |
| WHITE BALANCE | PERFORM WHITE BALANCE PROCESSING ON SENSOR-BY-SENSOR, LIGHT SOURCE-BY-LIGHT SOURCE BASIS | TAKE NO WHITE BALANCE<br>INPUT INFORMATION ON RESPECTIVE FEATURES OF SENSORS AND LIGHT SOURCES TO NAVIGATION APPARATUS |
| COLOR CORRECTION | ADJUST COLORS TO THOSE SUITABLE FOR HUMAN EYES | PERFORM NO COLOR CORRECTION<br>INPUT SPECTRAL INFORMATION ON SENSORS TO NAVIGATION APPARATUS |
| NOISE REDUCTION | PERFORM STRONG NOISE REDUCTION AS LONG AS KNOWN USEFUL INFORMATION IS NOT REMOVED | PERFORM WEAK OR NO NOISE REDUCTION<br>NAVIGATION APPARATUS RECOGNIZES NOISE AS NOISE |
| IMAGE ENHANCEMENT | ENHANCE FREQUENCY BAND TO ENHANCE KNOWN USEFUL INFORMATION | PERFORM NO IMAGE ENHANCEMENT |

FIG. 12

| STATUS | | FEEDBACK CONTENT (REQUEST FROM NAVIGATION APPARATUS TO PROCESSOR) | REMARKS |
|---|---|---|---|
| MANY MICROSCOPIC BLOOD VESSELS SHOWN IN WLI IMAGE | ⇒ | IMAGE OF, E.G., NBI USING LONG WAVELENGTHS FOR NAVIGATION APPARATUS | MICROSCOPIC BLOOD VESSELS IN SUPERFICIAL LAYER EASILY VIEWED IN SHORT-WAVELENGTH IMAGE |
| LITTLE INFORMATION ON BLOOD VESSELS IN WLI/NBI IMAGE | ⇒ | IMAGE OF, E.G., DRI USING SHORT WAVELENGTHS FOR NAVIGATION APPARATUS | DEEP BLOOD VESSELS EASILY VIEWED IN LONG-WAVELENGTH IMAGE |
| LITTLE MOVEMENT IN IMAGES | ⇒ | LOWER FPS OF IMAGE FOR HUMAN BEING AND INCREASE NUMBER OF TYPES OF ACQUIRED IMAGES FOR NAVIGATION APPARATUS | STRESS SMALL EVEN IF FPS OF IMAGE FOR HUMAN BEING IS LOWERED |
| MUCH MOVEMENT IN IMAGES | ⇒ | RAISE FPS OF IMAGE FOR HUMAN BEING AND DECREASE NUMBER OF TYPES OF ACQUIRED IMAGES FOR NAVIGATION APPARATUS OR ACQUIRE NO IMAGES FOR NAVIGATION APPARATUS | |
| IMAGE OF PERIPHERY DARK OR TOO BRIGHT (PART AROUND CENTER THAT HUMAN BEING PAYS ATTENTION TO IS ADEQUATELY BRIGHT) | ⇒ | SLIGHTLY BRIGHTENED/DARKENED IMAGES FOR NAVIGATION APPARATUS (PART AROUND CENTER THAT HUMAN BEING PAYS ATTENTION TO CAN BE TOO BRIGHT OR TOO DARK) | PROCESSOR APPROPRIATELY CORRECTS INTENSITY OF LIGHT OF LIGHT SOURCE AND EXPOSURE TIME OF IMAGER |

FIG. 14

| STATUS | FEEDBACKS WITH PRIORITY ORDER (REQUESTS FROM NAVIGATION APPARATUS TO PROCESSOR) | RESPONSE OF PROCESSOR |
| --- | --- | --- |
| FEW MICROSCOPIC BLOOD VESSELS IN WLI/NBI IMAGE PLUS, IMAGE OF PERIPHERY TOO DARK PLUS, MOVEMENT IN IMAGE LARGE | 1. DO NOT LOWER FPS OF IMAGE FOR DISPLAY | SECURE 30 FPS FOR IMAGE FOR DISPLAY |
| | 2. IMAGE OF, E.G., DRI USING LONG WAVELENGTHS FOR NAVIGATION APPARATUS | ACQUIRE DRI IMAGE WITH 2 FPS |
| | 3. SLIGHTLY BRIGHTENED IMAGES FOR NAVIGATION APPARATUS | DO NOT RESPOND TO REQUEST BECAUSE OF IMPOSSIBILITY TO RAISE FPS |

IMAGE PROCESSING APPARATUS, IMAGE PROCESSING METHOD, NAVIGATION METHOD AND ENDOSCOPE SYSTEM

CROSS REFERENCE TO RELATED APPLICATION

This application is a continuation application of PCT/JP2020/016037 filed on Apr. 9, 2020, the entire contents of which are incorporated herein by this reference.

BACKGROUND OF THE INVENTION

1. Field of the Invention

The present invention relates to an image processing apparatus for performing navigation when an image is observed, an image processing method, a navigation method and an endoscope system.

2. Description of the Related Art

Conventionally, navigation techniques that provide various types of support using an image processing technique have been developed. For example, in a medical field, e.g., insertion support that provides support for insertion of an endoscope and support for diagnosis of a result of estimation of a disease state are enabled by use of image processing techniques. For example, computer-aided diagnosis (CAD) in which support information for, e.g., provision of a quantitative criterion for determination, identification of a micro-structure to be focused on in diagnosis and a result of estimation of a disease state via image analysis has been developed. In an image processing apparatus that enables, e.g., CAD and/or insertion support such as above, various measures are taken to provide appropriate support to a surgeon.

For example, Japanese Patent Application Laid-Open Publication No. 2019-42156 discloses a technique that enables displaying two analysis results for first and second medical images in such a manner that the analysis results can be compared in terms of, e.g., position or area (size) to facilitate confirmation of the analysis results.

A real-time medical image acquired by, e.g., an endoscope is not only subjected to image processing for image analysis but also displayed on, e.g., a monitor, enabling providing very useful image information on, e.g., a diseased part to a surgeon in a surgical operation, an examination or the like.

SUMMARY OF THE INVENTION

An image processing apparatus of an aspect of the present invention includes a processor including hardware. The processor is configured to: set a first acquisition condition and a second acquisition condition for a video processor configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition; obtain an image analysis result by performing image analysis of an image acquired by the video processor; generate support information based on the image analysis result; and control switching between the first acquisition condition and the second acquisition condition according to the image analysis result.

An image processing method of an aspect of the present invention includes: setting a first acquisition condition and a second acquisition condition for a video processor configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition; obtaining an image analysis result by performing image analysis of an image acquired by the video processor; generating support information based on the image analysis result; and controlling switching between the first acquisition condition and the second acquisition condition according to the image analysis result.

A navigation method of an aspect of the present invention includes: setting a first acquisition condition including a display-purpose acquisition condition for acquiring an image for display at a frame rate for viewing, for a video processor configured to acquire a first image that is based on the display-purpose acquisition condition and a second image that is based on an analysis-purpose acquisition condition for acquiring an image for image analysis at a frame rate that is lower than the frame rate for viewing, in a mixed manner; setting a second acquisition condition including the display-purpose acquisition condition and the analysis-purpose acquisition condition, for the processor; obtaining an image analysis result by performing image analysis of an image acquired by the video processor; and controlling switching between the first acquisition condition and the second acquisition condition according to the image analysis result, and setting a third acquisition condition including the display-purpose acquisition condition and an analysis-purpose acquisition condition that is different from the analysis-purpose acquisition condition included in the second acquisition condition, for the video processor.

An endoscope system of an aspect of the present invention includes: an endoscope including an illumination apparatus and an image pickup apparatus, the endoscope being configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner; a video processor configured to make the endoscope acquire the first image and the second image based on at least one of the display-purpose acquisition condition or the analysis-purpose acquisition condition; and an image processing apparatus including a processor that includes hardware. The processor is configured to set a first acquisition condition including the display-purpose acquisition condition and a second acquisition condition including the display-purpose acquisition condition and the analysis-purpose acquisition condition and obtain an image analysis result by performing an image analysis of the image acquired by the video processor, generate support information based on the image analysis result, and control switching between the first acquisition condition and the second acquisition condition according to the image analysis result.

BRIEF DESCRIPTION OF THE DRAWINGS

FIG. 2 is a chart for describing needs for an image for display and an image for analysis;

FIG. 9 is a chart for describing examples of image processing by an image processing unit 12 based on a display-purpose acquisition condition and an analysis-purpose acquisition condition;

FIG. 12 is a chart for describing examples of an acquisition condition I3 based on a determination made by a determination unit 34;

FIG. 14 is a chart for describing a priority order of acquisition conditions for a plurality of requests;

DETAILED DESCRIPTION OF THE PREFERRED EMBODIMENTS

Embodiments of the present invention will be described in detail below with reference to the drawings.

First Embodiment

Figure 1:
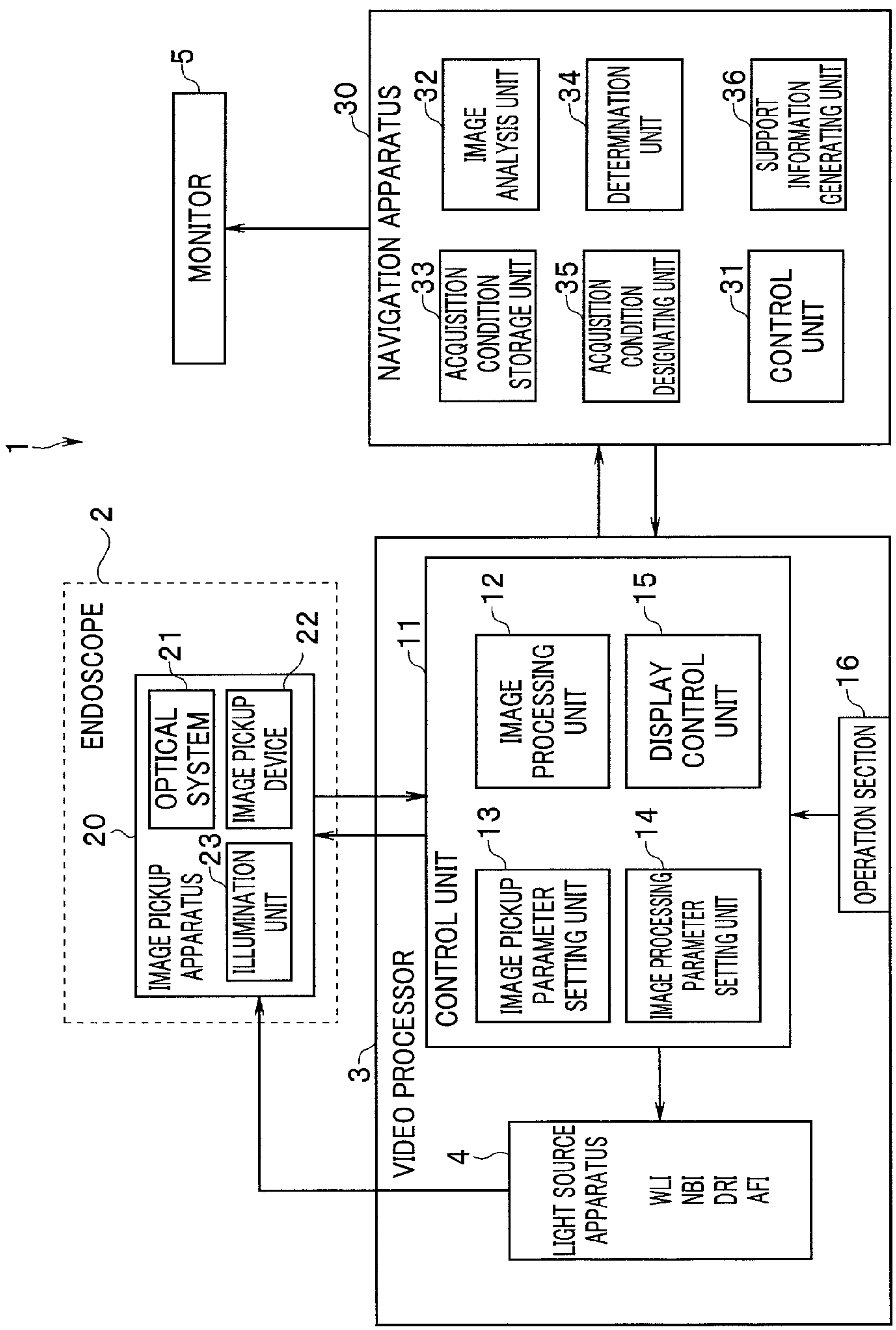
FIG. 1 is a block diagram illustrating a configuration of an endoscope system including an image processing apparatus according to a first embodiment of the present invention.

FIG. 1 is a block diagram illustrating a configuration of an endoscope system including an image processing apparatus according to a first embodiment of the present invention.

For example, acquiring an image to be used for image analysis for navigation and an image for display to be displayed on a monitor using separate image pickup apparatuses in an endoscope inevitably increases a size of a distal end portion of the endoscope. For such a reason, generally, for an image used for image analysis for navigation, an image for display is also used. However, an image for display is acquired under an acquisition condition suitable for display and may lack information necessary for image analysis. Note that an image for image analysis may be inferior in visibility and use of an image for image analysis as an image for display is not favorable. Accordingly, it is difficult to provide support based on a high-accuracy analysis result while displaying an easy-to-view endoscopic image. Note that in the present description, a high-accuracy analysis result is an analysis result that enables more effective support for a surgeon, and means not only a correct analysis result but also an analysis result of a type that is necessary for support from among various types of analysis results.

Therefore, in the present embodiment, very effective support for a surgeon can be delivered by enabling acquisition of a plurality of types of images, acquisition conditions for which are different, the plurality of types of images including an image for image display with good visibility and an image with good analyticity. Note that an image with good analyticity refers to an image that enables obtaining a high-accuracy analysis result.

Furthermore, in the present embodiment, in order to acquire an image with even better analyticity while maintaining image display with good visibility, it is possible to adaptively change an acquisition condition for an image. Note that FIG. 1 illustrates an endoscope system as an example but the present invention is not limited to this example and is applicable to any of various apparatuses for performing various types of work involving observation.

FIG. 2 is a chart for describing needs for an image for display and an image for analysis.

An image for display is an image for a human being to acquire necessary information by viewing the image displayed on a screen. On the other hand, an image for analysis is an image to be analyzed in a navigation apparatus. In consideration of a difference in quality of information processing between a human being and a computer, respective features suitable for an image for display and an image for analysis are different from each other.

As illustrated in FIG. 2, it is preferable that an image for display be an image with good visibility, the image including only useful information to the extent possible so that a human being can easily recognize. For example, with regard to image quality of an image for display, it is preferable that the image for display be an image with less noise, the image being subjected to gamma processing close to features of human eyes and being subjected to enhancement in a desired frequency band to be viewed.

On the other hand, an image for analysis is processed by, e.g., a computer, and thus, as an amount of information included in image information for analysis is larger, a more useful analysis result (high-accuracy analysis result) can be obtained. For example, even if an image for analysis includes image information in which a part other than a site of interest is conspicuous in terms of image quality, such image information has little adverse impact on an analysis result. Also, the image being subjected to, e.g., noise reduction, gamma processing and image enhancement processing may result in a lack of information necessary for analysis, and thus, it is better not to subject an image for analysis to these types of image processing.

Also, for example, in the case of special light observation using, e.g., NBI (narrow band imaging), which is effective for, e.g., observation of blood vessels in a mucous membrane, in consideration of image recognition ability of a human being, it is better that only one type of special light observation image or a normal light observation image only with special light observation image superimposed be displayed on a monitor screen.

On the other hand, even if a plurality of types of special light observation image signals are continuously inputted to a navigation apparatus, such input has no adverse impact on image analysis processing but rather enhances the possibility to obtain a useful analysis result from the plurality of types of image information.

While it is preferable that a frame rate of an image for display be 30 FPS or more from the perspective of a human being viewing the image for display, useful information can be obtained from an image for analysis even if a frame rate of the image for analysis is relatively low, for example, 1 FPS or less.

(Configuration)

Figure 3:
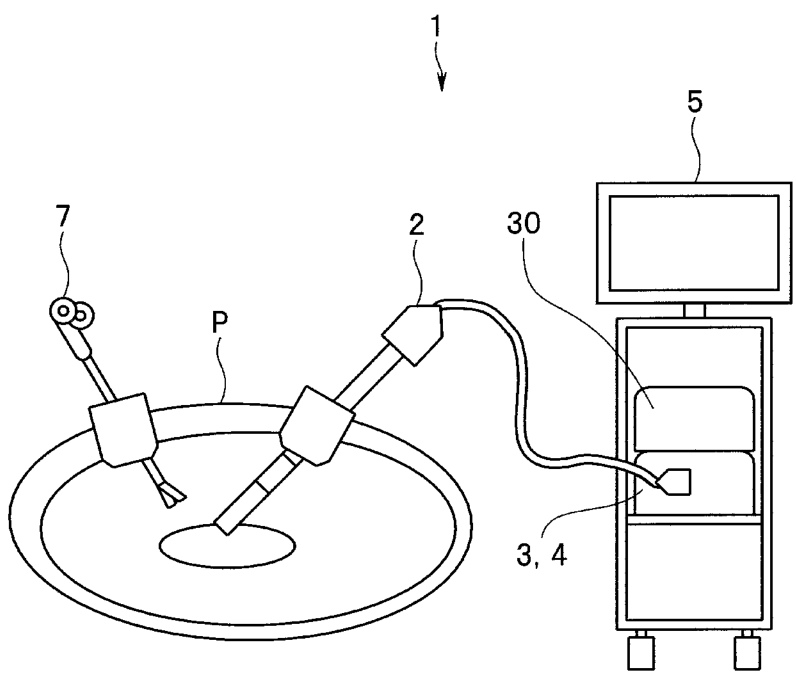
FIG. 3 is an explanatory diagram illustrating an example of usage of the endoscope system in FIG. 1.

FIG. 3 is an explanatory diagram illustrating an example of usage of the endoscope system in FIG. 1. An example of usage of the endoscope system will be described with reference to FIG. 3.

FIG. 3 illustrates an example in which treatment for the inside of an abdominal cavity of a subject P is performed using the endoscope system 1. The endoscope system 1 is an example of a laparoscopic surgery system. The endoscope system 1 mainly includes: an endoscope 2 (laparoscope) that picks up an image of the inside of the body cavity of the subject P and outputs an image pickup signal; a video processor 3 that controls driving of the endoscope 2 by the endoscope 2 being connected to the video processor 3 and acquires the image pickup signal of the image of the subject, the image being picked up by the endoscope 2, and subjects the image pickup signal to predetermined image processing; a light source apparatus 4 provided in the video processor 3, the light source apparatus 4 supplying predetermined illuminating light for illuminating the subject; a monitor 5 that displays an observation image according to the image pickup signal; and a navigation apparatus 30 that is an image processing apparatus for providing, e.g., diagnostic support, the navigation apparatus 30 being connected to the video processor 3.

FIG. 3 illustrates the endoscope 2 and a treatment instrument 7 that are inserted in the abdominal region of the subject P via respective trocars. The endoscope 2 is connected to the video processor 3 via a universal cord. The video processor 3, in which the light source apparatus 4 is incorporated, is configured to illuminate the inside of an abdominal cavity via the light source apparatus 4. The endoscope 2 is driven by the video processor 3 and picks up an image of the inside of the abdominal cavity of the subject P. The image picked up by the endoscope 2 is subjected to signal processing by the video processor 3 and then supplied to the navigation apparatus 30.

The navigation apparatus 30 provides the inputted picked-up image to the monitor 5 to display the picked-up image on the monitor 5 and generates support information via analytical processing of the picked-up image. The navigation apparatus 30 outputs the generated support information to the monitor 5 to display the generated support information on the monitor 5 as necessary, to provide support for a surgeon.

In the present embodiment, the navigation apparatus 30 is configured to acquire an image for image display with good visibility and also acquire an image effective for image analysis for support, by providing an instruction to the video processor 3 to set an image acquisition condition including at least one of an image pickup condition for image pickup via the endoscope 2 or an image processing condition for image processing via the video processor 3.

(Endoscope)

In FIG. 1, for the endoscope 2, any of various endoscopes such as a digestive endoscope and a laparoscope can be employed. The endoscope 2 includes an elongated insertion section to be inserted into, e.g., a body cavity of a subject, and an operation section arranged on the proximal end side of the insertion section, the operation section being grasped by a surgeon to perform an operation. A universal cord is provided in such a manner as to extend from a proximal end portion of the operation section, and the endoscope 2 is removably connected to the video processor 3 including the light source apparatus 4, via the universal cord.

An image pickup apparatus 20 is arranged in, for example, a distal end of the insertion section. The image pickup apparatus 20 includes an optical system 21, an image pickup device 22 and an illumination unit 23. The illumination unit 23 generates illuminating light by being controlled by the light source apparatus 4 and applies the generated illuminating light to a subject. The illumination unit 23 may include a non-illustrated predetermined light source, for example, an LED (light-emitting diode). In the present embodiment, the illumination unit 23 may include a plurality of light sources such as a light source that generates white light for normal observation, a light source that generates narrow band light for narrow band observation and a light source that generates infrared light of a predetermined wavelength. The illumination unit 23 has various irradiation modes and enables, e.g., switching of wavelengths of illuminating light, control of irradiation intensity and a temporal pattern of irradiation through the control performed by the light source apparatus 4.

Although FIG. 1 indicates an example in which the illumination unit 23 is provided inside the image pickup apparatus 20, a configuration in which the light source apparatus 4 generates illuminating light and the illuminating light is guided to a distal end of an endoscope 2 via a non-illustrated light guide and applied to a subject may be employed.

The optical system 21 may include, e.g., non-illustrated lenses and diaphragm for zooming or focusing, and also include a non-illustrated zooming (scaling) mechanism and a non-illustrated focusing and diaphragm mechanism. The illuminating light from the illumination unit 23 is applied to the subject and return light from the subject is guided to an image pickup surface of the image pickup device 22 through the optical system 21.

The image pickup device 22 includes, e.g., a CCD or a CMOS sensor, and acquires a picked-up image (image pickup signal) of a subject by performing photoelectric conversion of an optical image of the subject from the optical system 21. The image pickup apparatus 20 outputs the acquired picked-up image to the video processor 3.

The video processor 3 includes a control unit 11 that controls respective sections of the video processor 3, and the image pickup apparatus 20 and the light source apparatus 4. The control unit 11 and respective sections in the control unit 11 may be configured by a processor including, e.g., a CPU (central processing unit) or an FPGA (field-programmable gate array) and may be configured to operate according to a program stored in a non-illustrated memory and control the respective sections, and some or all of functions of the control unit 11 may be implemented by an electronic circuit of hardware.

(Light Source Apparatus)

The light source apparatus 4 controls the illumination unit 23 to generate white light and various types of special observation light. For example, the light source apparatus 4 may make the illumination unit 23 generate white light, NBI (narrow band imaging) light, DRI (dual red imaging) light, excitation light for AFI (auto-fluorescence imaging) (hereinafter, "AFI light"). White light is used as illuminating light for what is called WLI (white light imaging) observation (normal observation) (hereinafter, "WLI light"). NBI light is used for narrow band imaging, DRI light is used for dual red imaging and AFI light is used for fluorescence observation.

Note that the illumination unit 23 may include a plurality of types of LEDs, laser diodes, xenon lamps or the like to generate the aforementioned types of illuminating light, or may be configured to generate the aforementioned types of illuminating light using, e.g., white light and an NBI filter, a DRI filter and an AFI filter. A light intensity increase/decrease by the illumination unit 23 enables a change in exposure value during image pickup by the image pickup apparatus 20 and thus enables exposure control without being affected by saturation and low-luminance noise. For NBI light, blue light with a wavelength of $\lambda$=415 nm and green light with a wavelength of $\lambda$=540 nm may be generated.

(Video Processor)

The control unit 11 of the video processor 3 includes an image processing unit 12, an image pickup parameter setting unit 13, an image processing parameter setting unit 14 and a display control unit 15. The image pickup parameter setting unit 13 can set a status of illuminating light generated by the illumination unit 23 by controlling the light source apparatus 4. The image pickup parameter setting unit 13 can also set an optical system state of the optical system 21 and a driving state of the image pickup device 22 by controlling the image pickup apparatus 20.

In other words, the image pickup parameter setting unit 13 can set image pickup conditions including an optical condition and a driving condition for driving the image pickup device 22 at a time of image pickup by the image pickup apparatus 20. For example, the setting via the image pickup parameter setting unit 13 can be made to generate NBI light, DRI light, AFI light, etc., as illuminating light and control a wavelength, an intensity, etc., of the generated illuminating light. Also, the setting via the image pickup parameter setting unit 13 can be made to make the image pickup apparatus 20 be capable of outputting an image pickup signal in various modes, and enable control of, for example, a frame rate, a pixel count, pixel addition, a read area change, sensitivity switching and output with color signals discriminated from one another.

The image pickup signal outputted from the image pickup device 22 may be called "RAW data" and may be used as original data before image processing.

(Image Processing Unit)

The image processing unit 12 receives picked-up images (movie and still images) loaded from the image pickup apparatus 20 and performs predetermined signal processing, for example, color adjustment processing, matrix conversion processing, denoising processing, image synthesis, adaptive processing and other various types of signal processing, of the loaded picked-up images. The image processing parameter setting unit 14 is configured to set a processing parameter for image processing in the image processing unit 12.

Visibility of a picked-up image can be enhanced by image processing in the image processing unit 12. An analytical property of image analysis processing of a picked-up image can also be enhanced by image processing in the image processing unit 12. The image processing unit 12 can also convert what is called RAW data from the image pickup device into data of a particular form.

The display control unit 15 receives the picked-up images subjected to signal processing by the image processing unit 12. The display control unit 15 converts the picked-up images acquired by the image pickup apparatus 20 into an observation image that can be processed in the monitor 5 and outputs the observation image.

An operation section 16 is provided in the video processor 3. The operation section 16 may be configured by, for example, various buttons, dials and/or a touch panel, and receives an operation performed by a user and outputs an operational signal based on the instruction to the control unit 11. The operation section 16 may be configured in such a manner as to have handsfree capability and receive, e.g., a gesture input or a voice input and generate an operational signal. The control unit 11 is capable of controlling the respective sections according to an operational signal.

In the present embodiment, the settings by the image pickup parameter setting unit 13 and the image processing parameter setting unit 14 are controlled by the navigation apparatus 30.

(Navigation Apparatus)

The navigation apparatus 30 includes a control unit 31, an image analysis unit 32, an acquisition condition storage unit 33, a determination unit 34, an acquisition condition designating unit 35 and a support information generating unit 36. The control unit 31 may be configured by a processor using, e.g., a CPU or an FPGA or may be one configured to operate according to a program stored in a non-illustrated memory to control respective sections or may be one, some or all of functions of which are implemented by an electronic circuit of hardware. The entire navigation apparatus 30 or each of the respective component sections of the navigation apparatus 30 may also be configured by a processor using, e.g., a CPU or an FPGA, may be one configured to operate according to a program stored in a non-illustrated memory to control respective sections or may be one, some or all of functions of which are implemented by an electronic circuit of hardware.

In the acquisition condition storage unit 33, acquisition conditions for determining contents of settings by the image pickup parameter setting unit 13 of the video processor 3 and the image processing parameter setting unit 14 are stored. For example, in the acquisition condition storage unit 33, information relating to a type of and a setting for illuminating light that the light source apparatus 4 makes the illumination unit 23 emit (hereinafter referred to as "light source setting information"), information relating to driving of the optical system 21 (hereinafter referred to as "optical system setting information") and information relating to driving of the image pickup device 22 (hereinafter referred to as image pickup setting information) may be stored. Furthermore, in the acquisition condition storage unit 33, information for determining a content of image processing by the image processing unit 12 (hereinafter referred to as image processing setting information) may be stored.

In the acquisition condition storage unit 33, the light source setting information, the optical system setting information, the image pickup setting information and the image processing setting information (hereinafter, these pieces of information may also be referred to as "acquisition condition setting information") may be stored in combination. For example, acquisition condition setting information in an initial state, acquisition condition setting information in a predetermined observation mode and/or acquisition condition setting information corresponding to a predetermined analysis condition may be stored in advance.

The acquisition condition designating unit 35 is configured to be controlled by the control unit 31 to designate acquisition condition setting information read from the acquisition condition storage unit 33, for the image pickup parameter setting unit 13 and the image processing parameter setting unit 14. According to the designation by the acquisition condition designating unit 35, processing for e.g., an observation mode, a type of illuminating light and control relating to image pickup in the endoscope 2 and image processing in the video processor 3 is performed. Here, the acquisition condition designating unit 35 may be configured in such a manner as to generate acquisition condition setting information not stored in the acquisition condition storage unit 33 via control performed by the control unit 31 and output the acquisition condition setting information to the video processor 3. A configuration in which the acquisition condition storage unit 33 is omitted and the acquisition condition designating unit 35 generates acquisition condition setting information as necessary may also be employed.

For example, by the acquisition condition designating unit 35 designating light source setting information, the light source apparatus 4 designates which illuminating light of, e.g., WLI light, NBI light, DRI light and AFI light to use.

(WLI Light, NBI Light, DRI Light and AFI Light)

Figure 4:
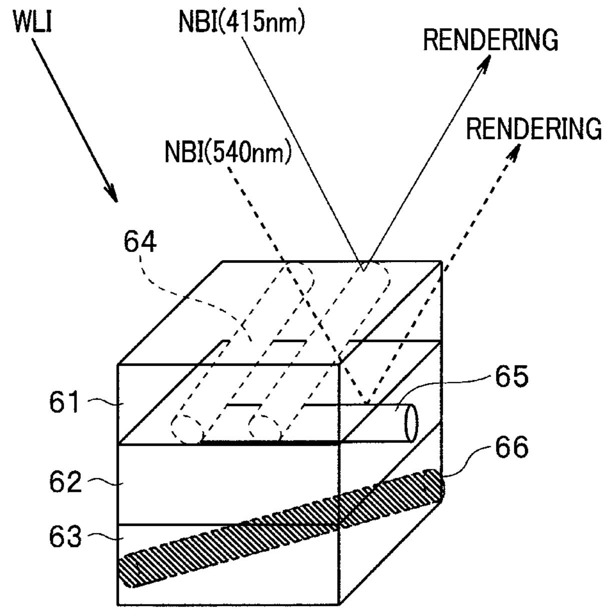
FIG. 4 is a diagram for describing a relationship between WLI light and NBI light provided from an endoscope according to the first embodiment and blood vessels in a mucous membrane of a subject.
Figure 5:
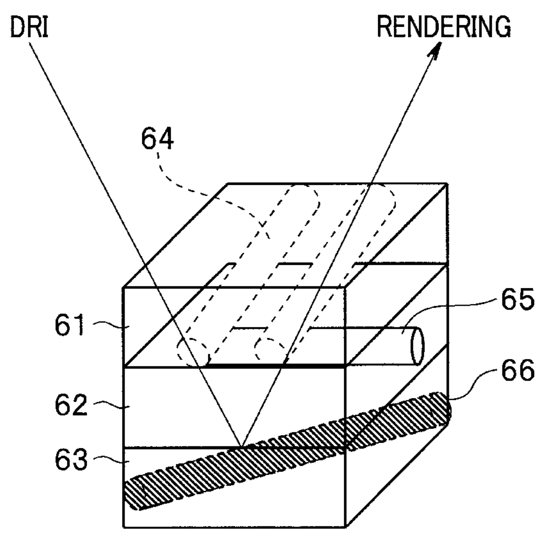
FIG. 5 is a diagram for describing a relationship between DRI light and blood vessels in a mucous membrane of a subject.

Here, WLI light, NBI light, DRI light and AFI light employed in the present embodiment will be described with reference to FIGS. 4 and 5. FIG. 4 is a diagram illustrating a relationship between WLI light and NBI light applied from the endoscope according to the first embodiment and blood vessels in a mucous membrane of a subject. FIG. 5 is a diagram illustrating a relationship between DRI light and blood vessels in a mucous membrane of a subject.

By WLI light (white light) being applied to a surface of a mucous membrane, blood vessels, etc., that are present in the mucous membrane can be reproduced in colors natural to a human being (doctor) on a monitor. On the other hand, where WLI light (white light) is used, capillary blood vessels and mucous membrane microscopic patterns in the superficial layer part of the mucous membrane are not always reproduced clearly enough to be recognized by the human being.

In the present embodiment, NBI (narrow band imaging) light including two wavelengths in narrow bands (blue light: 390 to 445 nm (415 nm in the present embodiment)/green light: 530 to 550 nm (540 nm in the present embodiment)) in which the light is easily absorbed in hemoglobin of blood may be employed to observe a mucous membrane.

As illustrated in FIG. 4, by the NBI light being applied, capillary blood vessels 64 in a mucous membrane superficial layer part 61 are clearly rendered as a result of the blue light (415 nm) in the NBI light being absorbed in the capillary blood vessels 64, and likewise, a blood vessel 65 in a layer 62 that is slightly deeper than the superficial layer part is rendered as a result of the green light (540 nm) being absorbed. Consequently, the capillary blood vessels and mucous membrane microscopic patterns in the mucous membrane superficial layer part 61 are displayed in an enhanced manner.

As described above, in the present embodiment, a special light observation may be performed with the wavelengths of the NBI light, which is narrow band light, set to other different wavelengths.

On the other hand, in the present embodiment, DRI (dual red imaging) light using light of a band narrowed to two long wavelengths (600 nm/630 nm) may be employed, and by the DRI light being applied to a subject, a blood vessel 66 or blood flow information in a part from a part from a mucous membrane deep layer to a submucosal layer (layer 63 in FIG. 5), which is difficult to view with normal light observation, may be displayed in an enhanced manner.

Furthermore, in the present embodiment, what is called AFI (auto-fluorescence imaging) in which predetermined excitation light for fluorescence observation is applied to a subject to display a neoplastic lesion and a normal mucous membrane in different colors in an enhanced manner is possible.

Not only such light source control, but also control of the optical system 21 and the image pickup device 22 can be performed based on acquisition condition setting information, and for example, exposure time of the image pickup device can be changed by setting of an acquisition condition. Exposure control enables eliminating effects of saturation and low-luminance noise.

(Example of Method for Acquiring a Plurality of Types of Images)

In the present embodiment, the acquisition condition designating unit 35 may generate acquisition condition setting information prescribing a display-purpose acquisition condition, which is a condition for acquiring an image for display with good visibility (hereinafter referred to as "display-purpose acquisition condition setting information") and acquisition condition setting information prescribing an analysis-purpose acquisition condition, which is a condition for acquiring an image for analysis with good analyticity in image analysis processing (hereinafter referred to as "analysis-purpose acquisition condition setting information"), in a mixed manner. For example, it is possible that in a predetermined first period, only display-purpose acquisition condition setting information is outputted and in a predetermined second period, display-purpose acquisition condition setting information and analysis-purpose acquisition condition setting information are outputted in a mixed manner.

When the display-purpose acquisition condition setting information is provided to the video processor 3, the video processor 3 controls at least one of the light source apparatus 4 (illumination unit 23), the optical system 21, the image pickup device 22 or the image processing unit 12 based on the display-purpose acquisition condition setting information in such a manner as to be capable of outputting an image for display with good visibility. When display-purpose acquisition condition setting information and analysis-purpose acquisition condition setting information are inputted in a mixed manner, the video processor 3 controls at least one of the light source apparatus 4 (illumination unit 23), the optical system 21, the image pickup device 22 or the image processing unit 12 based on the display-purpose acquisition condition setting information and the analysis-purpose acquisition condition setting information in such a manner that an image for display with good visibility and an image with good analyticity are outputted.

As described above, a display-purpose acquisition condition is an image pickup/illumination condition for making settings for bringing wavelengths of light from a light source close to natural light (daylight), performing visibility-oriented image processing of an image pickup result and setting, e.g., a frame rate in a continuity oriented manner so that a doctor feels natural when he/she looks for a diseased part under natural light or observes (mainly a surface of) a diseased part with the diseased part illuminated. An analysis-purpose acquisition condition is an image pickup/illumination condition, with an increased amount of effective information for image determination in preference to visibility for a doctor, for making analyticity-oriented settings for determining wavelengths of light from a light source in such a manner that light reaches not only a surface of a diseased part but also the inside of the diseased part, performing effective information amount-oriented image processing of an image pickup result for the purpose of analysis and setting, e.g., a frame rate in such a manner that a particular pattern or a feature of the image can easily be determined, in preference to continuity.

Figure 6:
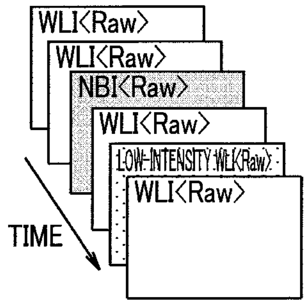
FIG. 6 is an explanatory diagram illustrating examples of picked-up images acquired by a video processor 3.
Figure 7:
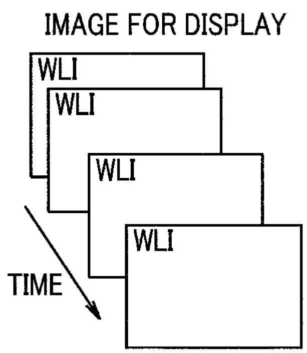
FIG. 7 is an explanatory diagram illustrating an example of an image outputted to a monitor 5.
Figure 8:
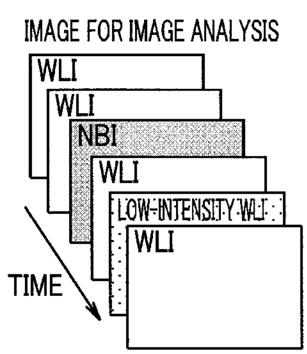
FIG. 8 is an explanatory diagram illustrating an example of an image supplied to an image analysis unit 32.

FIGS. 6 to 8 are explanatory diagrams illustrating respective examples of an image acquired by the video processor 3, an image being outputted to the monitor 5 and an image supplied to the image analysis unit 32, respectively, where the display-purpose acquisition condition setting information and the analysis-purpose acquisition condition setting information are inputted to the video processor 3 in a mixed manner.

FIG. 6 illustrates a series of frames obtained via image pickup by the image pickup device 22. In FIG. 6, WLI<Raw> indicates a picked-up image with a high frame rate (for example, 30 FPS or more), the picked-up image being obtained by image pickup using high-intensity WLI light as illuminating light. In addition, NBI<Raw> in FIG. 6 indicates a picked-up image with a low frame rate (for example, around 1 FPS), the picked-up image being obtained by image pickup using NBI light as illuminating light (narrow band imaging). Low-intensity WLI<Raw> indicates a picked-up image with a low frame rate (for example, 1 FPS), the picked-up image being obtained by image pickup using low-intensity WLI light as illuminating light.

A WLI<Raw> frame is used for generation of an image for display. Each of an NBI<Raw> frame and a low-intensity WLI<Raw> frame is used for generation of an image for analysis. Note that a WLI<Raw> frame may be used for generation of an image for analysis. Also, although not illustrated in FIG. 6, for a picked-up image for image analysis, DRI<Raw> frames obtained by image pickup using DRI light as illuminating light may be acquired with a low frame rate (around 1 FPS) or a picked-up image using excitation light for AFI observation may be acquired. As above, conditions for acquiring a result of image pickup of an object are changed for a same position of the image pickup, enabling acquiring useful information with a simple configuration with no need for complicated operation.

For example, a display image with good visibility can be expected to be obtained from a picked-up image with a high frame rate (for example, 30 FPS or more), the picked-up image being obtained by image pickup using high-intensity WLI light as illuminating light, and, e.g., a light source setting condition, an optical system setting condition and an image pickup setting condition for obtaining such an image are display-purpose acquisition conditions.

Also, for example, an image with good analyticity for image analysis can be expected to be obtained from images obtained by special light observation, such as NBI<Raw> frames, and, e.g., a light source setting condition, an optical system setting condition and an image pickup setting condition for obtaining such an image are analysis-purpose acquisition conditions. An image processing condition for obtaining an image with good visibility is a display-purpose acquisition condition and an image processing condition for obtaining an image with good analyticity is an analysis-purpose acquisition condition.

FIG. 9 is a chart indicating specific examples of display-purpose acquisition conditions and analysis-purpose acquisition conditions relating to image processing, the chart being provided for describing examples of conditions that can be met by image processing in the image processing unit 12. As illustrated in FIG. 9, for example, with regard to gamma processing from among types of image processing to be performed for an image pickup signal, the video processor 3 performs gamma processing suited to features of human eyes, according to the relevant display-purpose acquisition condition. The video processor 3 does not perform gamma processing, which is unnecessary for analytical processing, according to the relevant analysis-purpose acquisition condition. Likewise, as illustrated in FIG. 9, with regard to other image processing for, e.g., white balance, color correction, noise reduction and image enhancement, the video processor 3 distinguishes image processing for obtaining an image for display from image processing for obtaining an image for analysis according to the respective display-purpose acquisition conditions and the respective analysis-purpose acquisition conditions.

The image processing unit 12 of the video processor 3 acquires a WLI image for display with good visibility from a picked-up image of WLI<Raw> by performing signal processing according to the display-purpose acquisition condition setting information. The navigation apparatus 30 outputs the WLI image with good visibility, from among picked-up images from the video processor 3, to the monitor 5, as an image for display.

The above is illustrated in FIG. 7, and the control unit 31 of the navigation apparatus 30 extracts a WLI image from among images outputted from the video processor 3 and outputs the WLI image to the monitor 5. The example in FIG. 7 indicates that a WLI image obtained by image processing of WLI<Raw> frames from among the series of frames in FIG. 6 are extracted and supplied to the monitor 5. Note that the image pickup is performed in such a manner that a frame rate for the WLI image supplied to the monitor 5 becomes, for example, 30 FPS or more. For an image for visual confirmation, which is viewed to perform operation, the number of missing frames per unit time is minimized. However, this does not apply to, for example, a situation in which the image does not change.

Consequently, a picked-up image obtained by the image pickup apparatus 20 of the endoscope 2 is displayed on a display screen of the monitor 5. The image displayed on the monitor 5 is a WLI image with good visibility, and a surgeon can view an image in a range of field of view of the image pickup apparatus 20 in the form of an easy-to-view image on the display screen of the monitor 5.

A WLI image with good visibility may lack information useful for image analysis for navigation, because of the signal processing in the image processing unit 12. Therefore, as illustrated in FIG. 9, the video processor 3 stops many types of image processing for an image for analysis and adds information useful for image analysis, according to the analysis-purpose acquisition conditions. Consequently, output of an image for analysis useful for image analysis is enabled by the analysis-purpose acquisition condition setting information.

For example, capillary blood vessels and mucous membrane microscopic patterns in a mucous membrane superficial layer part, which have been described above, are difficult to discriminate based on a WLI image but is relatively easy to discriminate via image analysis using an NBI image obtained by image pickup using, e.g., NBI light. Therefore, the control unit 31 is configured to, for example, provide all of images outputted from the video processor 3, the images including an NBI image, to the image analysis unit 32 and make the image analysis unit 32 perform image analysis. FIG. 8 illustrates images supplied to the image analysis unit 32. Note that the control unit 31 may be configured to provide only images except a WLI image from among images outputted from the video processor 3 to the image analysis unit 32.

The image analysis unit 32 performs various image analyses for supporting the surgeon. The image analysis unit 32 performs an image analysis of a picked-up image inputted from the video processor 3 and obtains a result of the image analysis. The image analysis unit 32 acquires, for example, a result of image analysis relating to a direction of advancement of the insertion section of the endoscope 2 or a result of image analysis relating to a result of distinguishment of a lesion part. The image analysis result of the image analysis unit 32 is provided to the support information generating unit 36.

The support information generating unit 36 generates support information based on the image analysis result from the image analysis unit 32. For example, if a direction in which the insertion section is to be inserted is obtained from the image analysis result, the support information generating unit 36 generates support information indicating the insertion direction. Also, for example, if a result of distinguishment of a lesion part is obtained from the image analysis result, the support information generating unit 36 generates support information for presenting the distinguishment result to the surgeon. The support information generating unit 36 may generate support display data such as an image (support image) and/or a text (support text) to be displayed on the monitor 5, as support information. The support information generating unit 36 may also generate voice data for voice output from a non-illustrated speaker, as support information.

(Change of Acquisition Conditions)

Furthermore, in the present embodiment, the navigation apparatus 30 is configured to change an image acquisition condition based on a feature of an image used for analysis and/or an image analysis result including various types of information acquired from the image. The determination unit 34 determines whether or not to change an image acquisition condition and how to change the image acquisition condition. For example, if the determination unit 34 determines, based on an image analysis result, that the image analysis result is insufficient or a further detailed image analysis is necessary, the determination unit 34 provides an instruction to change an acquisition condition to an acquisition condition necessary for performing a desired image analysis, to the acquisition condition designating unit 35.

For example, the determination unit 34 may determine a change to a particular acquisition condition based on a particular criterion. For example, the determination unit 34 may determine an acquisition condition to be changed, by comparing a value included in an image analysis result, such as contrast information or histogram information, acquired from an image used for analysis, with a predetermined reference value. The determination unit 34 may also determine whether or not the image used for analysis includes a particular image feature or pattern, via, e.g., pattern matching, and based on a result of the determination, determine an acquisition condition to be set.

The determination unit 34 may be configured to provide an instruction to change an acquisition condition necessary for obtaining a desired analysis result, to the acquisition condition designating unit 35 according to not only an image analysis result but also an observation mode, a content of a procedure, etc.

(Operation)

Figure 10:
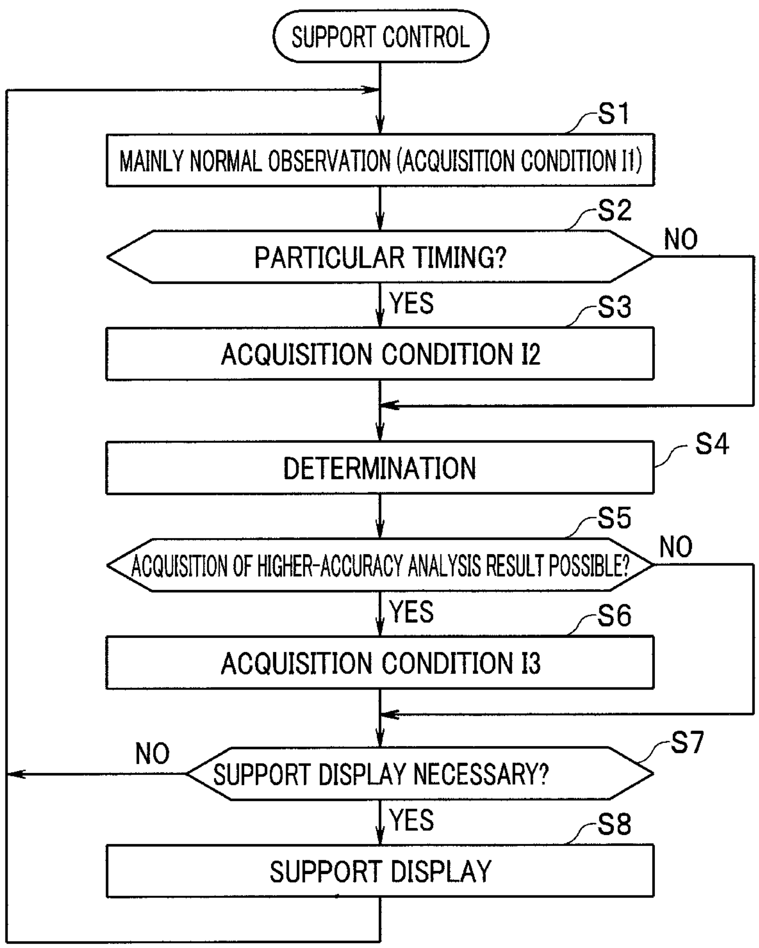
FIG. 10 is a flowchart for describing operation of the first embodiment.

Next, operation of the embodiment configured as above will be described with reference to FIGS. 10 to 14. FIG. 10 is a flowchart for describing operation of the first embodiment and FIG. 11 is an explanatory diagram for describing images acquired in a particular use case.

Figure 11:
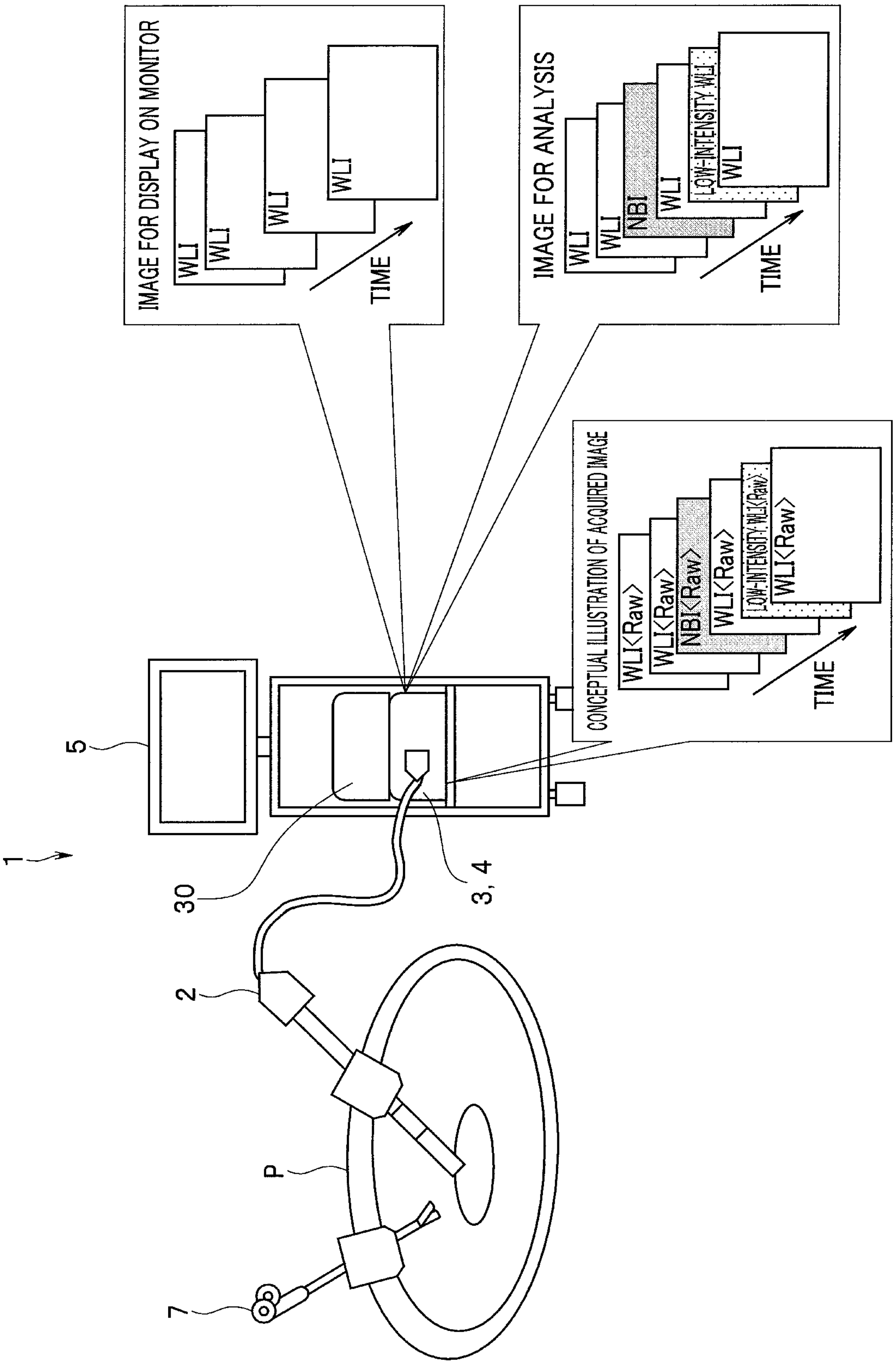
FIG. 11 is an explanatory diagram for describing images acquired in a particular use case.

The example in FIG. 11 indicates a situation of use that is similar to the situation of use in FIG. 3 and thus illustrates the endoscope 2 (rigid endoscope) inserted into a body cavity for observation of internal tissues and organ.

For example, immediately after power-on, the acquisition condition designating unit 35 of the navigation apparatus 30 reads display-purpose acquisition condition setting information in initial setting from the acquisition condition storage unit 33 and supplies the display-purpose acquisition condition setting information to the video processor 3. The display-purpose acquisition condition setting information enables setting of an acquisition condition for acquiring an image for display, and the image pickup parameter setting unit 13 in the control unit 11 of the video processor 3 sets parameters for the light source apparatus 4, the optical system 21 and the image pickup device 22 based on the display-purpose acquisition condition setting information.

Consequently, in step S1 in FIG. 10, normal observation is performed. Note that an acquisition condition I1 in FIG. 10 is, for example, an acquisition condition corresponding to the display-purpose acquisition condition setting information in the initial setting and is a condition determined in advance. According to the acquisition condition I1, for example, the light source apparatus 4 makes high-intensity WLI light be outputted from the illumination unit 23 and the control unit 11 drives the image pickup device 22 at a high frame rate (for example, 30 FPS or more) to make a picked-up image of WLI<Raw> be outputted from the image pickup apparatus 20.

The image processing parameter setting unit 14 of the control unit 11 sets an image processing parameter for the image processing unit 12 based on the display-purpose acquisition condition setting information. Consequently, for example, as illustrated in FIG. 9, the image processing unit 12 subjects the picked-up image from the image pickup apparatus 20 to, e.g., gamma processing suited to the features of human eyes, white balance processing, color correction suited to a feature of human eyes, noise reduction processing and image enhancement processing to generate a WLI image suitable for display.

The WLI image acquired by the image processing unit 12 is supplied to the navigation apparatus 30. The control unit 31 outputs the inputted WLI image to the monitor 5 as an image for display. Consequently, the WLI image with good visibility is displayed on the display screen of the monitor 5. A surgeon can reliably observe the internal tissues and organ, etc., inside the body cavity through the WLI image with good visibility on the display screen of the monitor 5.

In the example in FIG. 10, in step S2, the control unit 31 determines whether or not a particular timing for making a change from the acquisition condition I1 to an acquisition condition I2 is reached. Support via navigation apparatus 30 is not necessarily needed over an entire period from a start to an end of a surgical operation or an examination. In consideration of an amount of processing for image analysis in the navigation apparatus 30, it is deemed favorable to provide support via the navigation apparatus 30 only when the support is needed. Therefore, the control unit 31 makes switching from the acquisition condition I1, according to the display-purpose acquisition condition setting information, to the acquisition condition I2 including analysis-purpose acquisition condition setting information at a timing designated by an instruction from the surgeon or if the control unit 31 determines that a predetermined medical situation is reached. The acquisition condition I2 is a condition determined in advance. Note that each of the acquisition conditions I1, I2 can be set to an appropriate content via a user setting.

If the control unit 31 determines that, for example, a particular timing is reached according to an operation performed by the surgeon, the control unit 31 makes the processing transition to step S3 and provides an instruction for transition to the acquisition condition I2 to the acquisition condition designating unit 35. Note that if the control unit 31 determines that the particular timing is not reached, the control unit 31 makes the processing transition to step S4.

In step S3, the acquisition condition designating unit 35 reads acquisition condition setting information including the display-purpose acquisition condition setting information and analysis-purpose acquisition condition setting information and outputs the acquisition condition setting information to the video processor 3 to make transition to the acquisition condition I2. In other words, the acquisition condition I2 is a condition for acquiring not only an image for display but also an image for analysis by use of the display-purpose acquisition condition setting information and the analysis-purpose acquisition condition setting information.

In this case, the light source apparatus 4, the optical system 21 and the image pickup device 22 are controlled by the image pickup parameter setting unit 13 and the image processing parameter setting unit 14 to acquire a WLI<Raw> image at a frame rate of, for example, 30 FPS or more and acquire images suitable for image analysis. For example, as illustrated in FIG. 11, the image pickup apparatus 20 repeatedly acquire WLI<Raw>, WLI<Raw>, NBI<Raw>, WLI<Raw>, low-intensity WLI<Raw> and WLI<Raw> frames. In the example in FIG. 11, four frames in a series of six frames are WLI<Raw> frames acquired based on the display-purpose acquisition condition setting information and two frames are NBI<Raw> and low-intensity WLI<Raw> frames acquired based on the analysis-purpose acquisition condition setting information.

The image processing parameter setting unit 14 controls the image processing unit 12 based on the display-purpose acquisition condition setting information and the analysis-purpose acquisition condition setting information. Consequently, the image processing unit 12 performs signal processing of the WLI<Raw> frames based on the display-purpose acquisition condition setting information to acquire a WLI image. The image processing unit 12 performs, for example, no display-purpose signal processing for the NBI<Raw> and low-intensity WLI<Raw> frames based on the analysis-purpose acquisition condition setting information. Note that the image processing unit 12 converts NBI<Raw> frames and low-intensity WLI<Raw> frames into an NBI image and a low-intensity WLI image, respectively. The image processing unit 12 outputs the images to the navigation apparatus 30.

As illustrated in FIG. 11, the control unit 31 of the navigation apparatus 30 outputs the WLI image to the monitor 5 as an image for display and outputs the NBI image and the low-intensity WLI image to the image analysis unit 32. Note that the WLI image is provided also to the image analysis unit 32. The image analysis unit 32 performs an image analysis using the WLI image, the NBI image and the low-intensity WLI image to obtain a predetermined analysis result. For example, where diagnostic support is provided, desired analysis results of, e.g., determination of whether or not there is a lesion part candidate and/or differentiation of a lesion part are obtained by the image analysis unit 32.

The images analyzed in the image analysis unit 32 include an image obtained via special light observation such as an NBI image suitable for analysis and have not been subjected to image processing involving lack of information, and thus, the images have an amount of information sufficient for image analysis, enabling obtainment of a high-accuracy analysis result in the image analysis unit 32. The amount of the information is assumed to be an amount including information on respective pixels, the information being intended to derive something from an image, the information significantly indicating, e.g., a change in arrangement of the pixels, the amount of information being an amount necessary for identifying features of an object included in each of the images analyzed, such as a contrast, a spatial frequency, a gradation characteristic, a color change and distinguishability of wavelength difference in the color change.

In the present embodiment, subsequent to step S2 or S3, the processing in step S4 and the determination in step S5 are performed, and if a determination of "NO" is made in step S5, the processing transitions to step S7. In step S7, whether or not support display is necessary is determined. For example, if a lesion part candidate is found based on the image analysis result from the image analysis unit 32, the control unit 31 determines that support display is necessary, and makes the support information generating unit 36 generate support information. The support information generating unit 36 generates support information based on the analysis result from the image analysis unit 32.

For example, as support information where a lesion part candidate is found, the support information generating unit 36 may generate display data for displaying a mark (support display) indicating a position of the lesion part candidate on the image for display displayed on the display screen of the monitor 5. The control unit 31 provides the display data generated by the support information generating unit 36 to the monitor 5. Consequently, the mark indicating the position of the lesion part candidate is displayed on the image for display (observation image from the endoscope 2) displayed on the monitor 5 (step S8).

As described above, in the present embodiment, a WLI image with good visibility being displayed on the monitor 5 facilitates confirmation of, e.g., a diseased part and image analysis for support being performed using, e.g., an NBI image suitable for image analysis enables obtainment of a high-accuracy analysis result, enabling providing remarkably effective support for a surgeon. The configuration is made in such a manner that an image for analysis is acquired only when support is needed, enabling displaying an image for display with high image quality without unnecessary decrease in frame rate and also enabling preventing an unnecessary increase in amount of processing for image analysis. The image for display and the image for analysis are acquired based on image pickup signals from the image pickup apparatus 20, and thus, there is no need to dispose a plurality of image pickup apparatuses in a distal end portion of an insertion section of an endoscope, preventing an increase in size of the distal end portion, and there is also no need for high-performance hardware due to a significant increase in the amount of information processing.

(Adaptively Changing Acquisition Condition)

Furthermore, in the present embodiment, setting an acquisition condition I3 that changes according to a status enables higher-accuracy analysis. In step S4, based on the image for analysis and the image analysis result from the image analysis unit 32, the determination unit 34 determines whether or not to change the acquisition condition in order to acquire a higher-accuracy analysis result, and if the acquisition condition is to be changed, determine the acquisition condition. The determination unit 34 determines whether or not it is possible to obtain a higher-accuracy analysis result (step S5), and if it is possible, makes the acquisition condition designating unit 35 set an acquisition condition I3 for such purpose (step S6). Note that if the determination unit 34 determines that it is not possible to obtain a higher-accuracy analysis result, the determination unit 34 makes the processing transition to step S7.

In step S6, according to the result of the determination by the determination unit 34, the acquisition condition designating unit 35 reads the display-purpose acquisition condition setting information and the analysis-purpose acquisition condition setting information from the acquisition condition storage unit 33, and outputs the display-purpose acquisition condition setting information and the analysis-purpose acquisition condition setting information to the image pickup parameter setting unit 13 and the image processing parameter setting unit 14 as the acquisition condition I3. In other words, the acquisition condition I3 that has adaptively changed according to the output of the video processor 3 is fed back to the video processor 3. Note that the acquisition condition designating unit 35 may generate display-purpose acquisition condition setting information and analysis-purpose acquisition condition setting information according to the determination result from the determination unit 34 and output the display-purpose acquisition condition setting information and the analysis-purpose acquisition condition setting information, rather than outputting the information stored in the acquisition condition storage unit 33.

FIG. 12 is a chart for describing examples of the acquisition condition I3 based on a determination by the determination unit 34. In FIG. 12, the "status" column indicates information obtained from the analysis result from the image analysis unit 32 and the "feedback content" column indicates an acquisition condition I3 designated by the acquisition condition designating unit 35 based on the determination result from the determination unit 34.

Even when the image for display acquired based on the acquisition condition I1 is outputted, the image analysis unit 32 can perform image analysis using the image for display (WLI image). If the processing has transitioned from step S2 to step S4, the determination unit 34 makes determination using a result of analysis of the WLI image by the image analysis unit 32. For example, it is assumed that the image analysis unit 32 obtains blood vessel information relating to a mucous membrane from the analysis result of the WLI image. If the determination unit 34 determines that many blood vessels are shown in a mucous membrane superficial layer part, the determination unit 34 makes the acquisition condition designating unit 35 set an acquisition condition for acquiring an image for analysis such as an NBI image using long-wavelength illuminating light, as an acquisition condition I3.

An image for display using short-wavelength illuminating light (short-wavelength image) facilitates confirmation of microscopic blood vessels in the superficial layer of a tissue. Therefore, when many microscopic blood vessels are shown, the determination unit 34 determines, based on information on the blood vessels in the mucous membrane superficial layer part, that there may be some kind of malignant tumor, and in order to more clearly grasp a microscopic blood vessel structure in the mucous membrane superficial layer part, the determination unit 34 makes the acquisition condition designating unit 35 set an acquisition condition I3 for acquiring an NBI image as an image for analysis.

For example, when images for analysis (e.g., a WLI image and an NBI image) based on the acquisition condition I2 have been acquired, if an analysis result based on the images for analysis indicates that there is little information on microscopic blood vessels in the mucous membrane superficial layer part, the determination unit 34 makes the acquisition condition designating unit 35 set an acquisition condition I3 for acquiring a DRI image via short-wavelength DRI special light observation so that blood vessel information on blood vessels in a deeper part in the mucous membrane (for example, blood vessel information on blood vessels in the part from the deeper layer of the mucous membrane to the submucosal layer of the mucous membrane) can be obtained.

For example, the determination unit 34 sets an acquisition condition I3 for increasing/decreasing the frame rate of the image for display according to a magnitude of movement of an image of a diseased part of a subject in an image analyzed by the image analysis unit 32 and increasing/decreasing types of images in images for analysis.

For example, the determination unit 34 makes the acquisition condition designating unit 35 set an acquisition condition I3 for changing a luminance of an image for analysis according to information on a luminance of the periphery of a diseased part of a subject in an image analyzed by the image analysis unit 32. For example, if an image of the periphery of the diseased part of the subject is dark, the determination unit 34 makes the acquisition condition designating unit 35 set an acquisition condition I3 for increasing the luminance of the image for analysis, and if the image of the periphery of the diseased part of the subject is bright, the determination unit 34 makes the acquisition condition designating unit 35 set an acquisition condition I3 for decreasing the luminance of the image for analysis. Note that such control as above can be performed by appropriately correcting, e.g., an intensity of light of the light source or exposure time relating to the image pickup device. Consequently, support display is provided in step S8 using the image acquired based on the acquisition condition I3.

Although the flowchart in FIG. 10 indicates an example in which a change of an acquisition condition I3 is made only once, the determination unit 34 may be configured to repeatedly change the set content of the acquisition condition I3 as necessary.

FIG. 10 also indicates an example in which in a predetermined first period, only display-purpose acquisition condition setting information for acquiring an image for display is outputted, and in a predetermined second period responding to, for example, an operation performed by, e.g., a surgeon, an image for display and an image for analysis are acquired by mixing display-purpose acquisition condition setting information and analysis-purpose acquisition condition setting information. For example, it is possible that the surgeon sets the first period for a period of time during movement of the insertion section of the endoscope 2 to an observation target site and sets the second period at a point of time of a start of detection of a lesion part candidate after the distal end portion of the endoscope 2 reaching the observation target site.

Although an example in which an acquisition condition I1 is first generated using only display-purpose acquisition condition setting information for acquiring an image for display has been indicated, a display-purpose acquisition condition and an analysis-purpose acquisition condition may consistently be set from after power-on. For example, as an acquisition condition I1, a setting may be made so that, for example, one NBI<Raw> frame is acquired for every predetermined number of WLI<Raw> frames, a WLI image based on WLI<Raw> frames may be used as an image for display, and the WLI image and an NBI image based on NBI<Raw> frames may be used as images for analysis. In this case, a high-quality image can be displayed using the WLI image, which has a relatively high frame rate, and an analysis necessary for support can be performed with a processing load on the navigation apparatus 30 sufficiently reduced. Then, setting an acquisition condition 12 with an increased ratio of acquisition of an image for analysis based on an analysis result or an operation performed by a surgeon enables performing a high-accuracy analysis appropriate to support requested by the surgeon.

In other words, such image acquisition control as above proceeds as if such control is background processing without requiring special attention of the surgeon. Therefore, for example, accurate navigation is possible with no need for the surgeon to take the trouble of determining whether or not it is a timing requiring special observation using, e.g., NBI light, enabling instantaneous provision of effective support to the surgeon.

Figure 13:
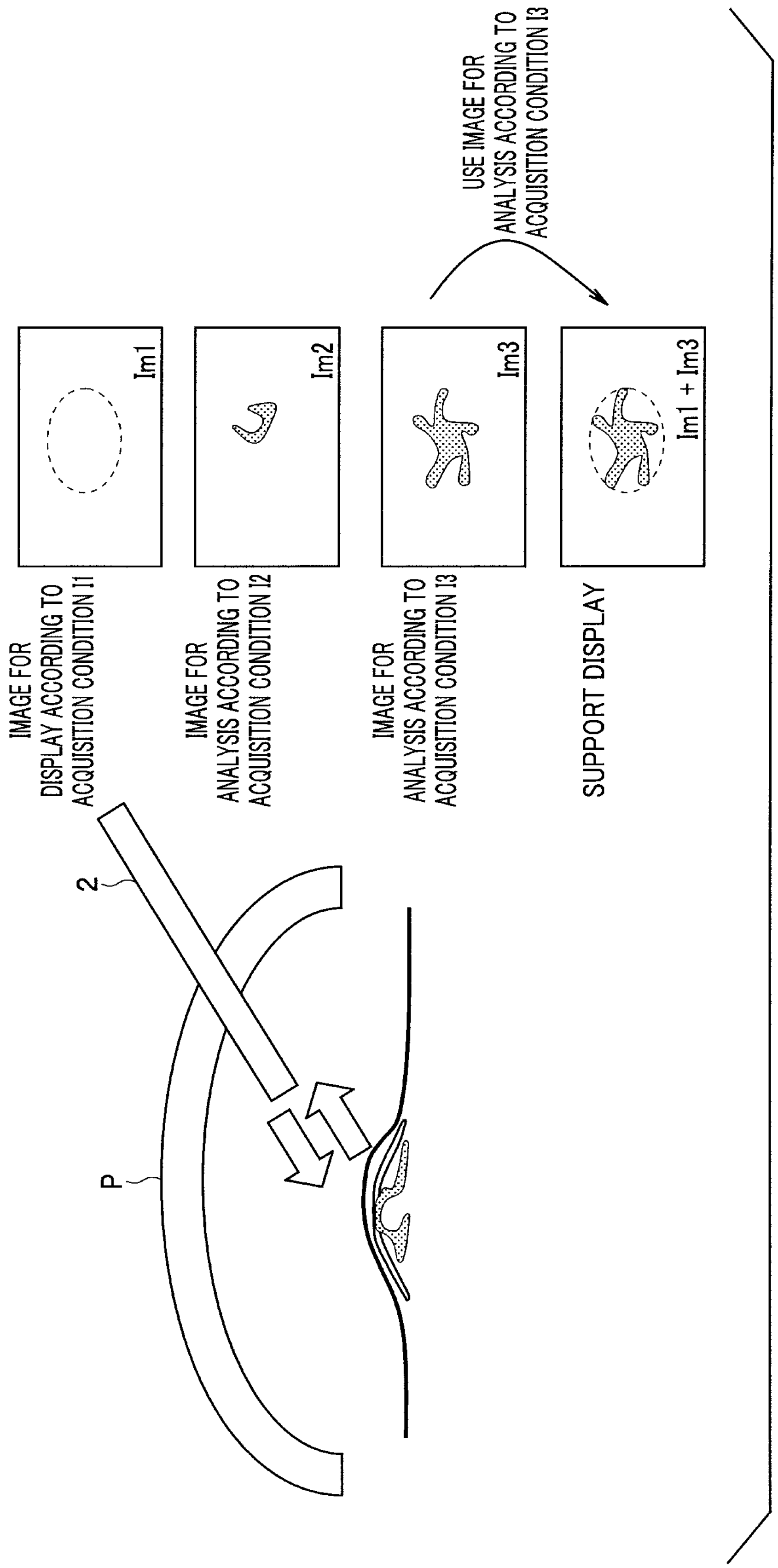
FIG. 13 is an explanatory diagram for describing support display.

FIG. 13 is an explanatory diagram for describing support display. FIG. 13 illustrates the endoscope 2 inserted in the body cavity P for observation of internal tissues and organs, and arrows indicate illuminating light outputted from the distal end of the rigid endoscope and reflected light of the illuminating light, and the reflected light enters the image pickup apparatus 20 of the endoscope 2.

(Image for Display Based on Acquisition Condition I1)

An image for display (Im1) obtained based on the acquisition condition I1 is an image obtained via white light imaging and is close to a result of observation under natural light that a human being is familiar with. In other words, in this example, the acquisition condition I1 is a condition for obtaining a visibility-oriented image for display. However, in image pickup based on the acquisition condition I1, components reflected from a surface of an object prevail and information on the inside of a tissue is relatively small, and thus, even if there is some kind of abnormality in the part surrounded by the dashed line, it may be difficult to find the abnormality.

(Image for Analysis Based on Acquisition Condition I2)

An image for analysis based on the acquisition condition I2 is an image (Im2) acquired based on image pickup conditions and image processing conditions including conditions for observation light that enables observation of the inside of a tissue, and thus, enables detection of an abnormality inside a tissue, which is not shown in a surface of the tissue of the body. In FIG. 13, a lesion part detected in the image is indicated by hatching. As described with reference to FIGS. 4 and 5, in comparison with an image acquired via normal white light imaging (image acquired based on the acquisition condition I1), use of an image acquired via special light imaging (image acquired based on the acquisition condition I2) enables obtainment of a high-accuracy analysis result.

(Image for Analysis Based on Acquisition Condition I3)

An image for analysis based on an acquisition condition I3 is an image (Im3) obtained using an acquisition condition resulting from the acquisition condition I2 being changed in order to obtain a higher-accuracy analysis result. In this case, as indicated by hatching in FIG. 13, a shape of the lesion part is clearer than a shape of the lesion part in the image Im2. As a result, an analysis result using the image (Im3) is often more accurate than an analysis result using the image (Im2).

(Support Display)

The support information generating unit 36 generates support information based on the higher-accuracy analysis result. In the example in FIG. 13, the support information is display data representing the shape of the lesion part. The control unit 31 makes display based on the support information be provided so as to be superimposed on the image for display (Im1). Furthermore, the support information generating unit 36 may generate display data for providing text display such as "lesion part found" in the vicinity of the position of the dashed line part as the support information. Consequently, an observer can confirm existence of the lesion part detected by the image analysis unit 32, on an image for display natural to human eyes, and the observer can also take measures such as re-examining the part via another method.

Note that various improvements and customizations of the method for providing support display via the support information generating unit 36 are possible. For example, FIG. 13 indicates an example in which support display based on the image for analysis based on the acquisition condition I3 is provided, but support display based on the image for analysis based on the acquisition condition I2 may be provided. The support information generating unit 36 may also make an image for analysis be displayed as it is as support display or may make a composite image based on an analysis result be displayed.

(Priority Order of Determination of Acquisition Conditions)

When the determination unit 34 changes an acquisition condition according to a status, it may be necessary to take a plurality of requests (acquisition conditions) into consideration. FIG. 14 is a chart for describing a priority order for a plurality of requests.

For example, a case where there are only a few microscopic blood vessels detected from a WLI image or an NBI image used for analysis by the image analysis unit 32, an image of the periphery is dark and movement of the image is large is assumed. In this case, the determination unit 34 makes the acquisition condition designating unit 35 generate an acquisition condition I3 for acquiring, e.g., a relatively bright DRI image using a long wavelength, as an image for analysis without decrease in frame rate of an image for display if possible.

However, there are cases where all of the requests cannot be met. Therefore, the determination unit 34 provides a priority order to the respective requests (conditions) to determine an acquisition condition I3. For example, the determination unit 34 determines a condition for preventing lowering of a frame rate of an image for display, as priority 1. The determination unit 34 determines a condition for acquiring, e.g., a DRI image using a long wavelength as an image for analysis as priority 2. The determination unit 34 determines a condition for acquiring a relatively bright image as priority 3.

In consideration of the priority order, the determination unit 34 provides an instruction to generate an acquisition condition I3 to the acquisition condition designating unit 35. For example, the acquisition condition designating unit 35 generates display-purpose acquisition condition setting information for maintaining a frame rate of WLI<Raw> frames to be used as an image for display at 30 FPS or more. For example, the acquisition condition designating unit 35 generates analysis-purpose acquisition condition setting information for acquiring DRI<Raw> frames for a DRI image, which is an image for analysis, at 2 FPS. For example, the acquisition condition designating unit 35 does not respond to the request of priority 3 in consideration of a maximum limit of frame rate enabling image pickup.

As described above, an acquisition condition generated with a priority order set for requests for the video processor 3 is fed back, enabling the video processor 3 to efficiently acquire images useful for both display and analysis. It is possible to reliably acquire an image according to an acquisition condition with endoscopes and video processors of various types that are different in performance and function.

As described above, the present embodiment enables acquisition of an image for image display with good visibility and an image with good analyticity and thus enables providing very useful support for various types of work while maintaining image display with good visibility. The present embodiment also enables adaptively changing an image acquisition condition and thus enables providing proper support according to a status.

Although FIG. 1 indicates an example in which the video processor 3 and the navigation apparatus 30 are configured separately from each other, it is clear that a configuration in which a navigation apparatus 30 is incorporated in a video processor 3 may be employed. The endoscope system is not limited to a laparoscopic surgery system but may be applied to an endoscope system using an ordinary flexible endoscope.

Also, e.g., analysis by the image analysis unit 32, determination by the determination unit 34 and generation of acquisition condition setting information by the acquisition condition designating unit 35 in the navigation apparatus 30 may be implemented by an AI (artificial intelligence) apparatus.

Second Embodiment

Figure 15:
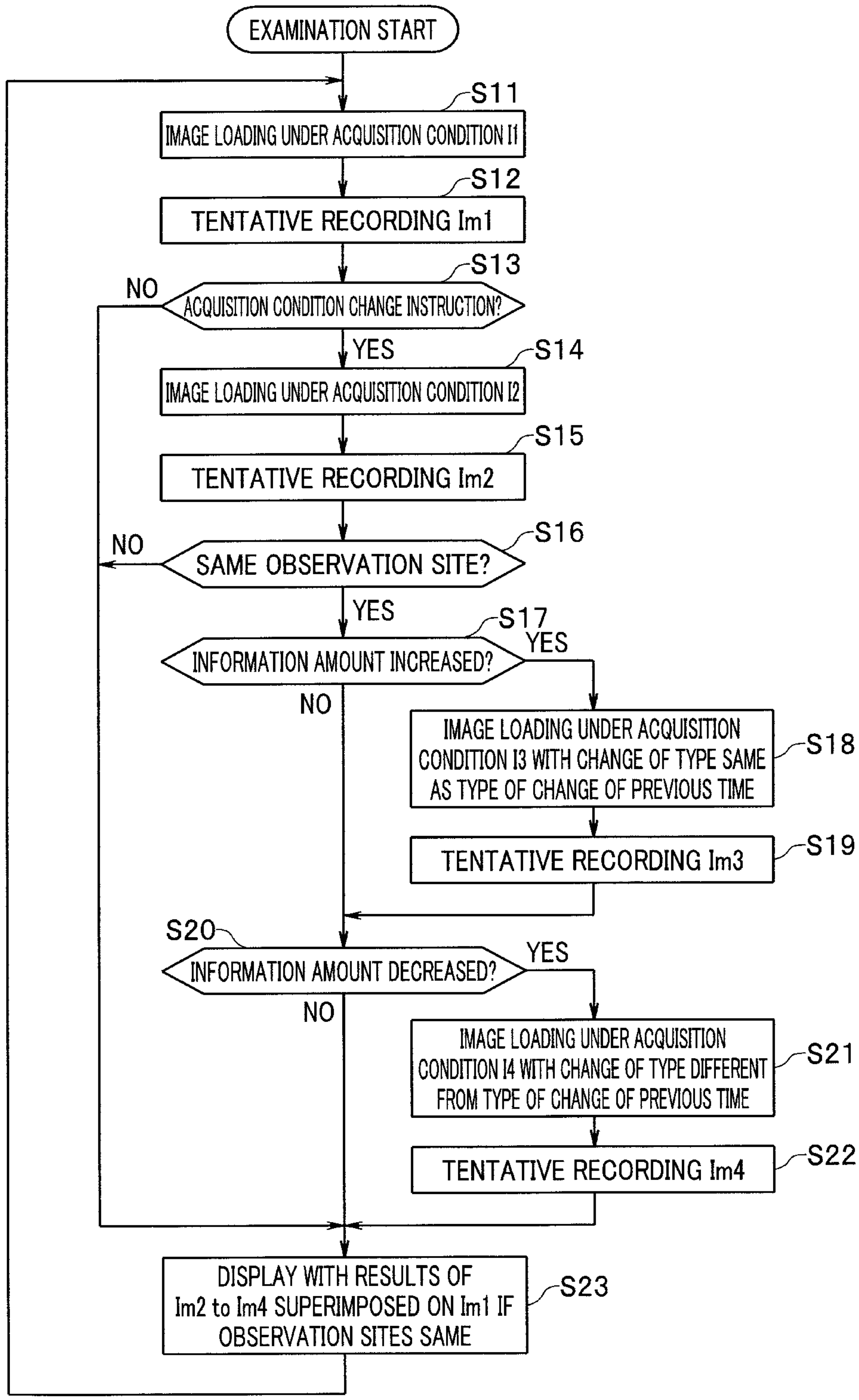
FIG. 15 is a flowchart illustrating an operation flow employed in a second embodiment.

FIG. 15 is a flowchart illustrating an operation flow employed in a second embodiment. A hardware configuration in the present embodiment is similar to the hardware configuration in FIG. 1, and thus, description of the hardware configuration is omitted.

In the first embodiment, an example in which an acquisition condition I3 is adaptively set when it is possible to obtain an analysis result that is higher in accuracy than analysis results based on the acquisition conditions I1, I2 has been described. In the present embodiment, when a change from an acquisition condition I1 to an acquisition condition I2 has been made, which of analysis results based on the acquisition conditions is higher in accuracy is determined. Note that, as described above, an analysis result being higher in accuracy means obtaining an analysis result that is more appropriate for support, and, for example, includes, e.g., a case where an amount of information obtained from an image has increased. In the present embodiment, if a determination result that a higher-accuracy analysis result can be obtained by a change of condition is obtained, a further change of a kind that is the same as a kind of the acquisition condition change is made, and if no such determination result is obtained, a change of a kind that is different from the kind of the acquisition condition change is made, enabling setting an optimum acquisition condition.

A further change of a kind that is the same as the kind of the acquisition condition change, for example, is a change that changes a wavelength of NBI light when a change from the acquisition condition I1 for acquiring normal light observation image to the acquisition condition I2 for acquiring an NBI image is made. A change of a kind that is different from the kind of the acquisition condition change means, for example, when a change from the acquisition condition I1 for acquiring a normal light observation image to the acquisition condition I2 for acquiring an NBI image is made, making an acquisition condition change for acquiring a DRI image instead of an NBI image.

For example, for a combination of the acquisition conditions I1 and I2, an acquisition condition I3 when a higher-accuracy analysis result has been obtained and an acquisition condition I3 when accuracy of an analysis result has lowered may be registered in advance in an acquisition condition storage unit 33. In this case, a determination unit 34 may be configured to provide an instruction regarding which of the acquisition conditions 13 stored in the acquisition condition storage unit 33 to read, to an acquisition condition designating unit 35, according to a result of determination of whether accuracy of the analysis result has been raised or lowered.

In step S11 in FIG. 15, image loading is performed based on an acquisition condition I1 determined in advance. For example, as illustrated in FIG. 13, an examination of the inside of a body cavity of a subject is started, an image is acquired via an endoscope 2 under the control of a control unit 11 in a video processor 3, and a picked-up image is supplied to a monitor 5 via a navigation apparatus 30. It is assumed that for the acquisition condition I1, for example, display-purpose acquisition condition setting information is employed and WLI<Raw> frames are acquired. An image processing unit 12 outputs a WLI image that is based on the WLI<Raw> frames to the navigation apparatus 30 and a control unit 31 supplies the WLI image to the monitor 5 to display the WLI image on a screen. Consequently, a WLI image with good visibility is displayed on the display screen of the monitor 5.

Note that the video processor 3 tentatively records the WLI image acquired based on the acquisition condition I1, in a non-illustrated recording apparatus as a picked-up image Im1 (step S12). An image analysis unit 32 of the navigation apparatus 30 obtains an analysis result via image analysis of the WLI image acquired based on the acquisition condition I1.

In step S13, the control unit 31 determines whether or not an acquisition condition change instruction has been made. As in the first embodiment, for example, it is possible to generate an acquisition condition change instruction via an instruction from a surgeon, and it is also possible that the determination unit 34 generates an acquisition condition change instruction based on an analysis result from the image analysis unit 32.

When an acquisition condition change instruction has been generated, the control unit 31 makes the acquisition condition designating unit 35 generate an acquisition condition I2 determined in advance. The acquisition condition designating unit 35 may read information on the acquisition condition I2 from the acquisition condition storage unit 33. Here, it is assumed that the acquisition condition I2 is a condition for acquiring a WLI image with a predetermined frame rate or more and, for example, an NBI image or the like. Consequently, for example, as illustrated in, e.g., FIG. 6, acquired images including WLI<Raw> frames and NBI<Raw> frames are acquired by the endoscope 2 (step S14). The image processing unit 12 generates a WLI image and an NBI image based on picked-up images from an image pickup apparatus 20 and outputs the WLI image and the NBI image to the navigation apparatus 30.

The image analysis unit 32 obtains an analysis result via image analysis of the WLI image and the NBI image acquired based on the acquisition condition I2. A support information generating unit 36 generates support information based on the analysis result. Note that the video processor 3 tentatively records the WLI image and the NBI image acquired based on the acquisition condition I2, in the non-illustrated recording apparatus as a picked-up image Im2 (step S15).

In step S16, the determination unit 34 determines whether or not images based on the acquisition conditions I1, I2 have been obtained for a same observation site. For example, the determination unit 34 can determine whether or not the images are images of a same observation site, based on the analysis results from the image analysis unit 32.

If the determination unit 34 determines that the respective images based on the acquisition conditions I1, I2 are images of a same observation site, in the next step S17, the determination unit 34 determines whether or not an amount of information (hereinafter, "amount of information" refers to amount of information representing features of an object included in images to be used for some kind of support or assistance) has increased. In other words, the determination unit 34 compares an amount of information in the image Im1 based on the acquisition condition I1, the image Im1 being obtained by application of WLI light to a certain area in the subject, and an amount of information in the image Im2 based on the acquisition condition I2, the image Im2 being obtained application of WLI light and NBI light to the same area, in terms of which amount of information is larger or smaller. The determination unit 34 determines which is an image including a relatively large amount of information between the amount of information (amount of information necessary for obtaining effective support) in the image Im1 and the amount of information (amount of information necessary for obtaining effective support) in the image Im2.

If the amount of information in the image based on the acquisition condition 12 has increased in comparison with the image based on the acquisition condition I1, the determination unit 34 determines that a more effective image can be acquired with an acquisition condition of a kind that is the same as a kind of the acquisition condition I2, and in step S18, provides an instruction to set an acquisition condition 13 of the same kind to the acquisition condition designating unit 35. Note that with regard to the parts "acquisition condition with a change of a same kind" in the figure, if an image with a sufficient amount of information has been obtained, no further change such as image acquisition or processing needs to be made.

As an acquisition condition I3 of a kind that is the same as the kind of the acquisition condition I2, for example, the acquisition condition designating unit 35 makes a change to information for acquiring an image using NBI light in a wavelength band that is different from a wavelength band designated by the acquisition condition I2. Consequently, in this case, for example, acquired images including WLI<Raw> frames with the predetermined frame rate or more and NBI<Raw> frames based on NBI light of a wavelength that is different from the wavelength of the previous time are acquired by the endoscope 2. The image processing unit 12 generates a WLI image and an NBI image based on the picked-up images from the image pickup apparatus 20 and outputs the WLI image and the NBI image to the navigation apparatus 30.

The image analysis unit 32 obtains an analysis result via image analysis of the WLI image and the NBI image based on the acquisition condition I2. The support information generating unit 36 generates support information based on the analysis result. The video processor 3 tentatively records the WLI image and the NBI image acquired based on the acquisition condition I3, in the non-illustrated recording apparatus as a picked-up image Im3 (step S19).

On the other hand, if the determination unit 34 determines in step S17 that the amount of information has not increased, the determination unit 34 makes the processing transition to step S20 and determines whether or not the amount of information has decreased. In other words, the determination unit 34 determines whether or not the amount of information in the image Im2 based on the acquisition condition I2, the image Im2 being obtained by application of WLI light and NBI light to the certain area in the subject, has decreased in comparison with the amount of information in the image Im1 based on the acquisition condition I1, the image Im1 being obtained by application of WLI light to the same area.

If the amount of information in the image based on the acquisition condition 12 has decreased in comparison with the amount of information in the image based on the acquisition condition I1, the determination unit 34 determines that an effective image can be obtained by an acquisition condition of a kind that is different from the kind of the acquisition condition I2, and in step S21, provides an instruction to set an acquisition condition I3 of a different kind to the acquisition condition designating unit 35.

The acquisition condition designating unit 35 makes a change to information for acquiring an image using DRI light instead of NBI light designated by the acquisition condition I2, as an acquisition condition I3 of a kind that is different from the kind of the acquisition condition I2. Note that the acquisition condition designating unit 35 may be configured to make a change to a condition for acquiring images using DRI light and AFI light, the image including NBI light in another wavelength band that is different from the wavelength band of the NBI light designated by the acquisition condition I2, as an acquisition condition I3 of a kind that is different from the kind of the acquisition condition I2. Furthermore, the acquisition condition designating unit 35 may be configured to involve a change in frame rate of the image pickup device 22 and/or change of various types of image processing by the image processing unit 12.

The image analysis unit 32 obtains an analysis result of image analysis of the respective images acquired based on the acquisition condition I3 of the kind that is different from the kind of the acquisition condition I2. The support information generating unit 36 generates support information based on the analysis result. The video processor 3 tentatively record the respective images acquired based on the acquisition condition I3 of the kind that is different from the kind of the acquisition condition I2, in the non-illustrated recording apparatus, as an image Im4 (step S22).

If determination of NO is made in step S16 or S20 or if the processing in step S22 ends, the control unit 31 proceeds to the next step S23, and if the images acquired based on the acquisition conditions I1 to I3 are images for a same observation site, the control unit 31 makes support information from the support information generating unit 36 based on the image analysis results of the images Im2 to Im4 be displayed in such a manner that the support information is superimposed on the image Im1 displayed on the monitor 5.

Note that FIG. 15 indicates an example in which setting of an acquisition condition I3 is made only once in either step S18 or S21, but steps S16 to S22 may be repeated until the amount of information enters a state in which the amount of information neither increases nor decreases. However, such repetition may take so much time and a condition cannot quickly be determined, and thus, the repetition may be made to end in a particular state. Of the two conditions, a better condition may be selected. As described above, execution of an image processing method including an image pickup step of picking up an image based on each of a plurality of different image pickup conditions to acquire a plurality of image pickup results, a comparison step of comparing the plurality of image pickup results acquired based on the different image pickup conditions, and an image pickup condition change step of changing a third image pickup condition based on an amount of information difference obtained from a result of the comparison enables presentation of high-accuracy support information based on an image obtained under a favorable condition.

As described above, the present embodiment also enables providing effects that are similar to the effects of the first embodiment.

Third Embodiment

Figure 16:
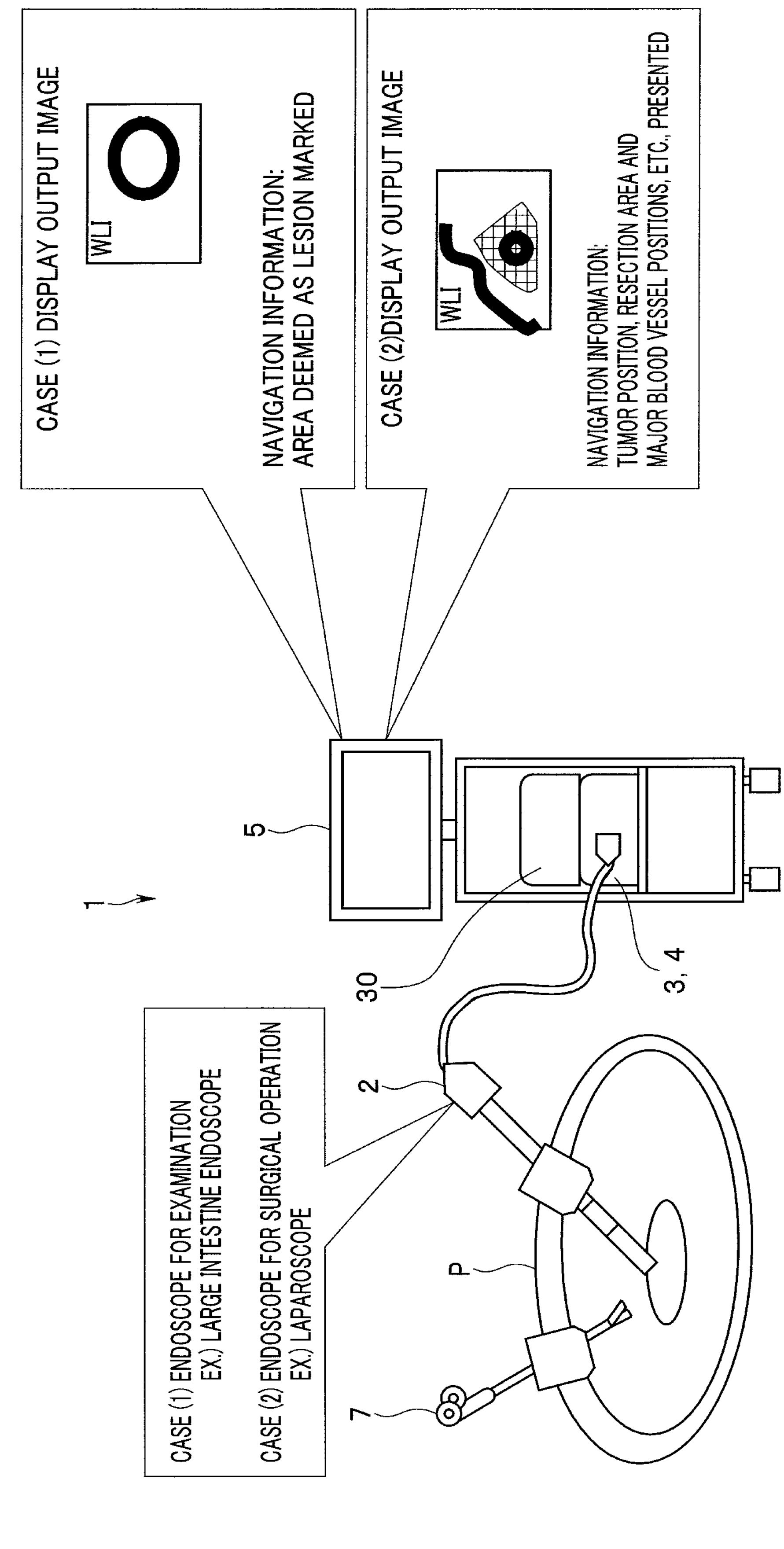
FIG. 16 is a block diagram illustrating a third embodiment.

FIG. 16 is a block diagram illustrating a third embodiment.

An endoscope system according to the third embodiment can be applied to many endoscope systems, for example, a system using an endoscope for examination such as a colonoscope and a system using an endoscope for surgical operation such as a laparoscope, and FIG. 16 illustrates an endoscope system 1 assumed to be a laparoscopic surgery system.

As illustrated in FIG. 16, the endoscope system 1 mainly includes: an endoscope 2 (laparoscope) configured to pick up an image of the inside of a body cavity of a subject P and output an image pickup signal; a video processor 3 to which the endoscope 2 is connected, the video processor 3 being configured to control driving of the endoscope 2, and acquire the image pickup signal relating to the subject, the image of the subject being picked up by the endoscope 2, and subject the image pickup signal to predetermined image processing; a light source apparatus 4 provided inside the video processor 3, the light source apparatus 4 being configured to supply predetermined illuminating light to be applied to the subject; a monitor 5 configured to display an observation image according to the image pickup signal; and a navigation apparatus 30 connected to the video processor 3. In the case of a system using an endoscope for examination, although a type of an endoscope 2 is different, other components are similar to the components in the example illustrated in FIG. 16.

Respective configurations of the respective components in the endoscope system 1 of the third embodiment, that is, the endoscope 2, the video processor 3, the light source apparatus 4, the monitor (display) 5 and the navigation apparatus 30, are similar to the configurations in the first embodiment, and thus, detailed description of the configurations here is omitted.

When the endoscope system 1 of the third embodiment is, for example, a system using an endoscope for examination, the navigation apparatus 30 is configured to output an image with high-accuracy marking of a lesion site to the monitor (display) 5.

More specifically, in the case of a navigation apparatus 30 in an endoscope system for examination, the endoscope system using a colonoscope, as illustrated in FIG. 16, the navigation apparatus 30 outputs, for example, an image with high-accuracy marking of an area deemed as a lesion site based on respective image information (image-for-display information and image-for-analysis information) with no lack, the image information being provided from the video processor 3 in such a manner as above, to the monitor (display) 5 and provides the image to a surgeon as navigation information.

On the other hand, in the case of a system using an endoscope for surgical operation, a navigation apparatus 30 is configured to output an image presenting information effective for a procedure to a monitor (display) 5.

More specifically, in the case of a navigation apparatus 30 in an endoscope system for surgical operation, the endoscope system using a laparoscope, as illustrated in FIG. 16, based on respective image information (image-for-display information and image-for-analysis information) with no lack, the image information being provided from a video processor 3 in such a manner as above, the navigation apparatus 30 outputs information, for example, a position of a tumor, a resection area and a position of a major blood vessel, to a monitor (display) 5 and provides the information to a surgeon as navigation information.

Like the endoscope system of the third embodiment, the present invention provides an endoscope system 1 using any of various endoscopes, in which as image information to be provided from a video processor 3 to a navigation apparatus 30 in such a manner as above, image-for-analysis information for the navigation apparatus 30 is provided in addition to image-for-display information, and recognition processing is performed in the navigation apparatus 30 using the image information with no lack, enabling any type of endoscope system 1 to provide useful navigation information (support information) to a surgeon.

As the endoscope system of the third embodiment, as described above, an endoscope system for examination and an endoscope system for surgical operation have been taken as examples, but the endoscope system of the third embodiment is not limited to these examples, and the endoscope system of the third embodiment may be applied to an endoscope system using another type of endoscope.

From among the techniques described here, much of the control and functions mainly described with reference to the flowcharts can be set by a program and the above control and functions can be implemented by the program being read and executed by a computer. The program can entirely or partly be recorded or stored on a portable medium such as a flexible disk, a CD-ROM or the like or a non-volatile memory or a storage medium such as a hard disk or a volatile memory, as a computer program product, and can be distributed or provided at a time of delivery of the product or through the portable medium or a communication channel. A user can easily implement the image processing apparatus of the present embodiment by downloading the program through a communication network and installing the program in a computer or installing the program from a medium with the program recorded to the computer.

The present invention is not limited to the above-described embodiments as they are, and in the practical phase, can be embodied with components modified without departing from the gist of the invention. Also, various aspects of the invention can be formed by an appropriate combination of a plurality of components disclosed in the respective embodiments described above. For example, some components of all the components indicated in an embodiment may be deleted. Furthermore, components in different embodiments may appropriately be combined. Here, although the above description has been provided taking an example of medical use, it should be understood that the invention is applicable to devices for commercial or industrial purposes. For example, a navigation apparatus can be replaced with an apparatus that detects some kind of abnormality in the industrial field or the security field other than the medical field and support information can be restated as information urging awareness. For industrial applications, the present invention is applicable to, e.g., assistance for determining quality of those that are moving down on a plant line or during work using an in-process camera, an awareness urging guide in monitoring using a wearable camera or a robot camera or obstacle determination using an in-vehicle camera. For commercial cameras, use for various types of guiding is possible. For microscopes, observation using light source or image processing switching has been known and application of the present invention is effective.

What is claimed is:

1. An image processing apparatus comprising:
a processor including hardware, the processor being configured to:
set a first acquisition condition and a second acquisition condition for a video processor configured to acquire:
a first image that is based on a display-purpose acquisition condition for acquiring an image for display at a frame rate for viewing; and
a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition;
obtain an image analysis result by performing image analysis of one or more of the first image and the second image acquired by the video processor, the image analysis result including blood vessel information relating to blood vessels located in a mucosal deep layer and submucosa;
generate support information based on the image analysis result; and
control switching between the first acquisition condition and the second acquisition condition according to the image analysis result.

2. An image processing method comprising:
setting a first acquisition condition and a second acquisition condition for a video processor configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition;
obtaining an image analysis result by performing image analysis of an image acquired by the video processor, the image analysis result including blood vessel information relating to blood vessels located in a mucosal deep layer and submucosa, wherein the display-purpose acquisition condition includes information that enables acquiring the image for display at a rate that is equal to or higher than a predetermined frame rate;
generating support information based on the image analysis result; and
controlling switching between the first acquisition condition and the second acquisition condition according to the image analysis result.

3. An image processing apparatus comprising:
one or more processors, each comprising hardware, the one or more processors being configured to set first, second and third acquisition conditions for a video processor configured to:
acquire a first image based on acquisition conditions for display at a frame rate according to the acquisition conditions for display for acquiring an image suitable for display; and
acquire a combination of the first image and a second image or a third image based on acquisition conditions for analysis for acquiring an image suitable for image analysis at a frame rate lower than the frame rate according to the acquisition conditions for display, wherein the one or more processors are configured to set:
the first acquisition conditions including the above-mentioned acquisition conditions for display;
the second acquisition conditions including the above-mentioned acquisition conditions for display and acquisition conditions for analysis; and
the third acquisition conditions including the above-mentioned acquisition conditions for display and acquisition conditions for analysis in which a wavelength of illumination light is different from that of the above-mentioned second acquisition conditions;
an image analysis device configured to perform image analysis on each of the first to third images acquired by the video processor, to obtain image analysis results including blood vessel information relating to blood vessels located in a mucosal deep layer and submucosa;
a support information generation device configured to generate support information based on the image analysis results of the image analysis device; and
the one or more processors are further configured to switch from the first acquisition condition to the second acquisition condition based on the image analysis results and to further switch from the second acquisition condition to the third acquisition condition.

4. The image processing apparatus according to claim 3, wherein the video processor is configured to set at least one parameter from among a first parameter for control of at least one of an optical system or an image pickup device of an image pickup apparatus, a second parameter for control of illuminating light for a target of image pickup by the image pickup apparatus and a third parameter for signal processing of the first and second images, based on at least one of the display-purpose acquisition condition or the analysis-purpose acquisition condition.

5. The image processing apparatus according to claim 3, wherein the display-purpose acquisition condition includes information that enables acquiring the image for display at a rate that is equal to or higher than a predetermined frame rate.

6. The image processing apparatus according to claim 4, wherein the analysis-purpose acquisition condition includes information that enables limiting the wavelength band of the illuminating light to a predetermined band.

7. The image processing apparatus according to claim 3, wherein: the display-purpose acquisition condition includes information for making the video processor perform signal processing for display, for one or more of the first image and the second image; and the analysis-purpose acquisition condition includes information for preventing the video processor from performing signal processing for display.

8. The image processing apparatus according to claim 3, wherein:

the first and second acquisition conditions are prescribed conditions; and the third acquisition condition is a condition that adaptively changes.

9. The image processing apparatus according to claim 3, wherein the one or more processors are configured to determine the third acquisition condition based on a comparison between a value included in the image analysis result and a predetermined reference value.

10. The image processing apparatus according to claim 3, wherein the one or more processors are configured to determine the third acquisition condition based on a comparison between the image analysis result of an image acquired based on the first acquisition condition and the image analysis result of an image acquired based on the second acquisition condition.

11. An endoscope system comprising:

an endoscope comprising an illumination apparatus and an image pickup apparatus; and the image processing apparatus of claim 3.

12. The image processing apparatus according to claim 3, wherein, under the display-purpose acquisition condition, the frame rate is at least 30 frames per second, and under the analysis-purpose acquisition condition, the frame rate is at least 1 frame per second.

13. A non-transitory computer-readable storage medium storing a program for image processing, the program being configured to cause a computer to execute:

setting a first acquisition condition and a second acquisition condition for a video processor configured to acquire a first image that is based on a display-purpose acquisition condition for acquiring an image for display at a frame rate for viewing and a second image that is based on an analysis-purpose acquisition condition for acquiring an image for image analysis at a frame rate that is lower than the frame rate for viewing, in a mixed manner, the first acquisition condition including the display-purpose acquisition condition, the second acquisition condition including the display-purpose acquisition condition and the analysis-purpose acquisition condition;

obtaining an image analysis result by performing image analysis of an image acquired by the video processor, the image analysis result including blood vessel information relating to blood vessels located in a mucosal deep layer and submucosa, wherein the display-purpose acquisition condition includes information that enables acquiring the image for display at a rate that is equal to or higher than a predetermined frame rate;

generating support information based on the image analysis result; and controlling switching between the first acquisition condition and the second acquisition condition according to the image analysis result.

* * * * *